United States Patent
Mande et al.

(10) Patent No.: US 11,610,649 B2
(45) Date of Patent: Mar. 21, 2023

(54) METHOD AND SYSTEM FOR IDENTIFICATION OF KEY DRIVER ORGANISMS FROM MICROBIOME / METAGENOMICS STUDIES

(71) Applicant: Tata Consultancy Services Limited, Mumbai (IN)

(72) Inventors: Sharmila Shekhar Mande, Pune (IN); Pranjal Chandrakar, Pune (IN); Kuntal Kumar Bhusan, Pune (IN)

(73) Assignee: TATA CONSULTANCY SERVICES LIMITED, Mumbai (IN)

( * ) Notice: Subject to any disclaimer, the term of this patent is extended or adjusted under 35 U.S.C. 154(b) by 731 days.

(21) Appl. No.: 15/476,527

(22) Filed: Mar. 31, 2017

(65) Prior Publication Data

US 2018/0032668 A1 Feb. 1, 2018

(30) Foreign Application Priority Data

Jul. 30, 2016 (IN) .............................. 201621026138

(51) Int. Cl.
| | |
|---|---|
| *G16B 25/10* | (2019.01) |
| *G16B 25/00* | (2019.01) |
| *G16B 40/00* | (2019.01) |
| *G16H 50/30* | (2018.01) |
| *G16H 50/20* | (2018.01) |
| *G16B 5/00* | (2019.01) |
| *C12Q 1/689* | (2018.01) |
| *G06F 5/01* | (2006.01) |
| *G06F 17/18* | (2006.01) |

(52) U.S. Cl.
CPC ............ *G16B 25/10* (2019.02); *C12Q 1/689* (2013.01); *G06F 5/01* (2013.01); *G06F 17/18* (2013.01); *G16B 5/00* (2019.02); *G16B 25/00* (2019.02); *G16B 40/00* (2019.02); *G16H 50/20* (2018.01); *G16H 50/30* (2018.01); *C12Q 2600/158* (2013.01)

(58) Field of Classification Search
None
See application file for complete search history.

(56) References Cited

U.S. PATENT DOCUMENTS

| | | | |
|---|---|---|---|
| 2012/0185227 A1 | 7/2012 | Nikolskaya et al. | |
| 2014/0207385 A1* | 7/2014 | Martin | G16B 5/00 702/19 |
| 2015/0211078 A1* | 7/2015 | Apte | C12Q 1/6888 506/2 |

FOREIGN PATENT DOCUMENTS

| | | |
|---|---|---|
| CA | 2911416 A1 | 11/2014 |
| WO | WO 2011022660 A1 | 2/2011 |
| WO | WO 2014005094 A1 | 1/2014 |

OTHER PUBLICATIONS

Faust et al. Netherlands Annual Ecology Meeting (NAEM), 2013.*
Faust, K. et al., "Microbial Co-occurrence Relationships in the Human Microbiome", PLOS Computational Biology, PLoS Comput Biol., pp. 1-22, Jul. 2012.
Faust, K. et al., "Microbial interactions: from networks to models", Nature Reviews Microbiology, Macmillan Publishers Limited, pp. 538-550, Aug. 2012.

* cited by examiner

*Primary Examiner* — Michael L Borin
(74) *Attorney, Agent, or Firm* — Finnegan, Henderson, Farabow, Garrett & Dunner LLP

(57) ABSTRACT

A system and method for identification of key driver responsible for bringing changes in a microbial population is provided. The method involves construction of microbial association networks with each microbial taxa as nodes and their associations as edges and subsequent identification of crucial 'driver' nodes involved in the studied disease progression. While comparing a particular node between two networks, this method takes individual nodes and their associations into account as well as the identity of their interacting partners. A taxon in the diseased state with an altered set of associations while still being increasingly important for the whole network necessarily holds a key significance in microbial interplay. Using this rationale, this methodology computes a score to quantify this change for each node and calculates its statistical significance. Subsequently, 'driver' nodes are identified using the score coupled with other network parameters and a critical score for the 'driver' nodes is calculated to quantify its importance.

6 Claims, 8 Drawing Sheets

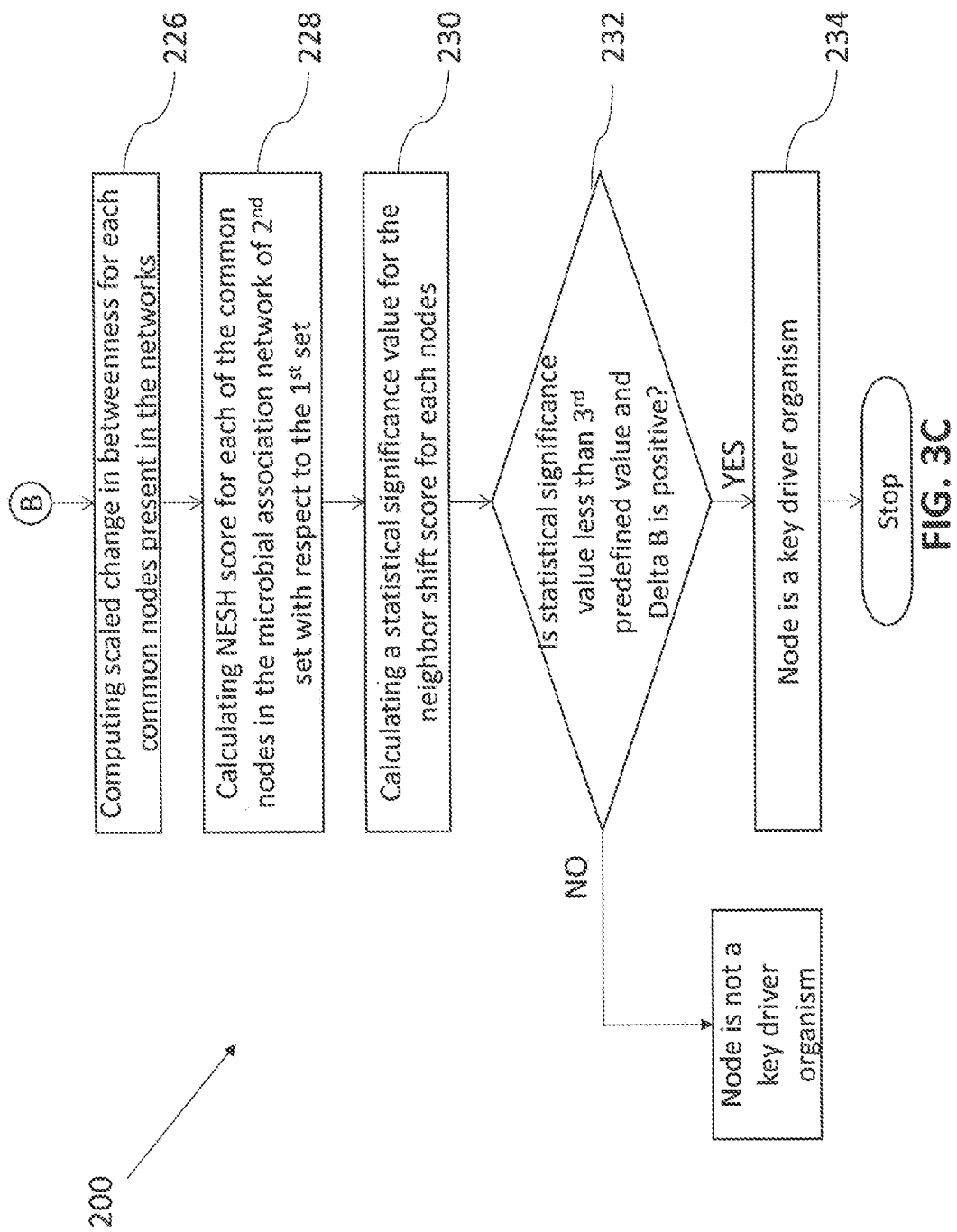

| SCENARIO | Control neighbor set | Disease neighbor set | JACCARD | OCHIAI | NESH | JACCARD | OCHIAI | NESH |
|---|---|---|---|---|---|---|---|---|
| Able to assign a different score when control node has no neighbors vs changes in neighbors from control to disease | None | e,f,g,h,i,j,k | 0 | NA | -1.7 | 0 | 1 | 1 |
|  | None | e,f,g,h | 0 | NA | -1.4 |  |  |  |
|  | a,b,c,d | e,f,g,h,i,j,k | 0 | 0 | -1.33636 |  |  |  |
| Able to differentiate extent of changes where control has no neighbours but diseased has different neighbours | None | e,f,g,h,i,j,k | 0 | NA | -1.7 | 0 | 0 | 1 |
|  | None | e,f,g,h | 0 | NA | -1.4 |  |  |  |
| Able to differentiate changes when exclusive neighbors of variable numbers emerge in disease from a similar set of control neighbours | a,b,c,d | e,f,g,h,i,j,k | 0 | 0 | -1.33636 | 0 | 0 | 1 |
|  | a,b,c,d | e,f,g,h | 0 | 0 | -0.9 |  |  |  |
| Capture changes correctly when neighbors emerge in disease from a set of control neighbours with variable overlaps | a,m,n | a,b,c,d,e,f | 0.125 | 0.23570226 | -1 | 0 | 0 | 1 |
|  | a,b,c | a,b,c,d,e,f,g,h | 0.375 | 0.61237244 | -0.75 |  |  |  |
|  | a,b,c,d | e,a,f,c,g,h,d | 0.375 | 0.56694671 | -0.525 |  |  |  |
| Capture changes correctly when lower count of neighbours is present in disease with respect to control with/without overlap | a,b,c,d,e,f | m,n,o | 0 | 0 | -0.63333 | 1 | 1 | 1 |
|  | a,b,c,d,e,f | a,m,n | 0.125 | 0.23570226 | -0.325 |  |  |  |
|  | a,b,c,d,e,f | a,b,c | 0.5 | 0.70710678 | 0.5 |  |  |  |
| Sensitive to directional change | a,m,n | a,b,c,d,e,f | 0.125 | 0.23570226 | -1 | 0 | 0 | 1 |
|  | a,b,c,d,e,f | a,m,n | 0.125 | 0.23570226 | -0.325 |  |  |  |

FIG. 5

METHOD AND SYSTEM FOR IDENTIFICATION OF KEY DRIVER ORGANISMS FROM MICROBIOME / METAGENOMICS STUDIES

CROSS-REFERENCE TO RELATED APPLICATIONS AND PRIORITY

The present application claims priority from Indian non-provisional specification no. 201621026138 filed on 30 Jul. 2016, the complete disclosure of which, in its entirety is herein incorporated by references.

TECHNICAL FIELD

The embodiments herein generally relates to the field of detection of key driver micro-organism, and, more particularly, to a method and system for the identification of key driver organisms responsible for bringing changes in a microbial population corresponding to a micro-biome associated disease.

BACKGROUND

In the recent times, major advances has been observed in the field of genomics and other high throughput biology. Various ecological studies have been performed to analyze the DNA samples to detect driver organisms responsible for a disease. Generally, the samples are collected from several different environments and abundances of different microbial species in the respective environments are analyzed. In some cases, these environments can represent micro-biota associated with human body such as lung, gut, skin etc. Here, different environments can exemplify different health conditions for example, healthy and diseased. In such cases, comparison between two microbial association networks holds key information to reveal 'driver' species which have a critical role in onset and progression of the disease.

Current methods intended to identify the microbial basis of a disease rely on construction of matrices of microbial abundances. For example, a study aiming to associate one or more microbe to a disease would identify the statistically differentially abundant ones in the diseased state with respect to the healthy. However, the combined effect of the mutual association and inhibition within the residing microbial communities plays an even bigger role in determining particular characteristics which cannot be quantified by these differential abundance analyses. Available methods for quantifying these changes in microbial association patterns rely on creating microbial association networks from the abundance data and subsequently compare their network properties. However, in most of the cases, these global graph property measures fail to scrutinize changes endured by individual nodes in the two representative networks In another method, one can compare two association networks by comparing local network properties like degree and betweenness. However, these local network properties mainly depend on the number of edges passing through a particular node. Such analyses however only provide a qualitative measure of the compared properties and completely ignore the constituent members. Similarly, global properties also cannot be used directly to compare two networks in a situation where the number of nodes and edges in the two networks are comparative but connections between nodes are entirely different, i.e., in case of network rewiring. In other words, two networks may look very similar while comparing their traditional network properties yet may be very different owing to the fact that individual nodes have an entirely different set of edges in the two environments. Special analysis methods are hence required to analyze such networks.

Methods used to calculate differentially abundant genera between two conditions (e.g., control and disease) rely only on the genera abundance information and completely ignore the inter-microbial interactions. However, the combined effect of the mutual association and inhibition within the residing microbial communities are known to play important roles in influencing the disease state and propagation, which gets completely ignored by such methodologies.

SUMMARY

The following presents a simplified summary of some embodiments of the disclosure in order to provide a basic understanding of the embodiments. This summary is not an extensive overview of the embodiments. It is not intended to identify key/critical elements of the embodiments or to delineate the scope of the embodiments. Its sole purpose is to present some embodiments in a simplified form as a prelude to the more detailed description that is presented below.

In view of the foregoing, an embodiment herein provides a system for identification of key driver responsible for bringing changes in a microbial population. The system comprises an input module, an extractor, a sequencer, a memory and a processor. The input module receives a sample from a first set of individuals and a second set of individuals. The extractor extracts DNA samples from the sample from the first and the second set of individuals. The sequencer sequences each of the DNA samples to generate a plurality of DNA sequences. The processor coupled with the memory, wherein the processor configured to perform following steps. The processor filters and processes the plurality of DNA sequences for removing the low quality DNA sequences and non-essential DNA fragments using a filtering module. Further, the processor creates two matrices of microbial abundance profile of the plurality of DNA sequences corresponding to the first set and the second set of individuals. Each matrix of microbial abundance profile includes abundances of microbial organisms corresponding to each members belonging to the microbial population. The processor normalizes each matrix using a normalization method. The microbial organisms are represented in each matrix as a plurality of nodes. The processor further generates a microbial association network for the first set and the second set using the normalized matrices. The processor computes Jaccard node index and Jaccard edge index between the microbial association network of first set and the microbial association network of the second set. The processor identifies if the Jaccard node index is higher than a first predefined value and Jaccard edge index is lower than a second predefined value. The processor quantifies the network rewiring based on the identified Jaccard node index and Jaccard edge index. The processor computes a scaled change in betweenness for each of the nodes in the microbial association network of second set with respect to the microbial association network of the first set. The processor calculates a neighbor shift score for each of the nodes in the microbial association network of the second set with respect to the microbial association network of the first set using a predefined formula. The processor calculates a statistical significance value for the neighbor shift score for each of the nodes. Finally the processor identifies a node as the key driver if the statistical significance value of its neighbor shift score is less than a third predefined value and the scaled change in betweenness is positive.

In another aspect, an embodiment provides a processor implemented method for identification of key driver responsible for bringing a change in a microbial population. Initially, a sample is retrieved from a first set of individuals and a second set of individuals. In the next step, DNA samples are extracted from the sample from the first and the second set of individuals. Further, each of the DNA samples are sequenced using a sequencer to generate a plurality of DNA sequences. In the next step, the plurality of DNA sequences are filtered and processed for removing the low quality DNA sequences and non-essential DNA fragments. In the next step, two matrices of microbial abundance profile of the plurality of DNA sequences are created corresponding to the first set and the second set of individuals. Each matrix of microbial abundance profile includes abundances of microbial organisms corresponding to each members belonging to the microbial population. Further, each matrix are normalized using a normalization method. The microbial organisms are represented in each matrix as a plurality of nodes. In the next step, a microbial association network is generated for the first set and the second set using the normalized matrices. Further, Jaccard node index and Jaccard edge index are computed between the microbial association network of first set and the microbial association network of the second set. In the next step, it was identified that if the Jaccard node index is higher than a first predefined value and Jaccard edge index is lower than a second predefined value. If the condition is satisfied, the network rewiring is quantified based on the identified Jaccard node index and Jaccard edge index. In the next step, a scaled change in betweenness is calculated for each of the nodes in the microbial association network of the second set with respect to the microbial association network of the first set. Further, a neighbor shift score is calculated for each of the nodes in the microbial association network of the second set with respect to the microbial association network of the first set using a predefined formula. In the next step, a statistical significance value is calculated for the neighbor shift score for each of the nodes. Finally, a node is identified as the key driver if the statistical significance value of its neighbor shift score is less than a third predefined value and the scaled change in betweenness is positive.

In another embodiment, a non-transitory computer-readable medium having embodied thereon a computer program for identification of key driver responsible for bringing a change in a microbial population. Initially, a sample is retrieved from a first set of individuals and a second set of individuals. In the next step, DNA samples are extracted from the sample from the first and the second set of individuals. Further, each of the DNA samples are sequenced using a sequencer to generate a plurality of DNA sequences. In the next step, the plurality of DNA sequences are filtered and processed for removing the low quality DNA sequences and non-essential DNA fragments. In the next step, two matrices of microbial abundance profile of the plurality of DNA sequences are created corresponding to the first set and the second set of individuals. Each matrix of microbial abundance profile includes abundances of microbial organisms corresponding to each members belonging to the microbial population. Further, each matrix are normalized using a normalization method. The microbial organisms are represented in each matrix as a plurality of nodes. In the next step, a microbial association network is generated for the first set and the second set using the normalized matrices. Further, Jaccard node index and Jaccard edge index are computed between the microbial association network of first set and the microbial association network of the second set. In the next step, it was identified that if the Jaccard node index is higher than a first predefined value and Jaccard edge index is lower than a second predefined value. If the condition is satisfied, the network rewiring is quantified based on the identified Jaccard node index and Jaccard edge index. In the next step, a scaled change in betweenness is calculated for each of the nodes in the microbial association network of the second set with respect to the microbial association network of the first set. Further, a neighbor shift score is calculated for each of the nodes in the microbial association network of the second set with respect to the microbial association network of the first set using a predefined formula. In the next step, a statistical significance value is calculated for the neighbor shift score for each of the nodes. Finally, a node is identified as the key driver if the statistical significance value of its neighbor shift score is less than a third predefined value and the scaled change in betweenness is positive.

It should be appreciated by those skilled in the art that any block diagram herein represent conceptual views of illustrative systems embodying the principles of the present subject matter. Similarly, it will be appreciated that any flow charts, flow diagrams, state transition diagrams, pseudo code, and the like represent various processes which may be substantially represented in computer readable medium and so executed by a computing device or processor, whether or not such computing device or processor is explicitly shown.

BRIEF DESCRIPTION OF THE DRAWINGS

The embodiments herein will be better understood from the following detailed description with reference to the drawings, in which:

FIGS. 3A-3C is a flowchart illustrates the steps involved for the identification of key driver organisms responsible for bringing changes in a microbial population according to an embodiment of the present disclosure;

FIG. 5 is a table showing evaluation of NESH score under various scenarios encountered in real work networks according to an embodiment of the present disclosure.

The Figures depict various embodiments of the present invention for purposes of illustration only. One skilled in the art will readily recognize from the following discussion that alternative embodiments of the structures and methods illustrated herein may be employed without departing from the principles of the invention described herein.

DETAILED DESCRIPTION OF EMBODIMENTS

The embodiments herein and the various features and advantageous details thereof are explained more fully with reference to the non-limiting embodiments that are illustrated in the accompanying drawings and detailed in the following description. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

Figure 1:
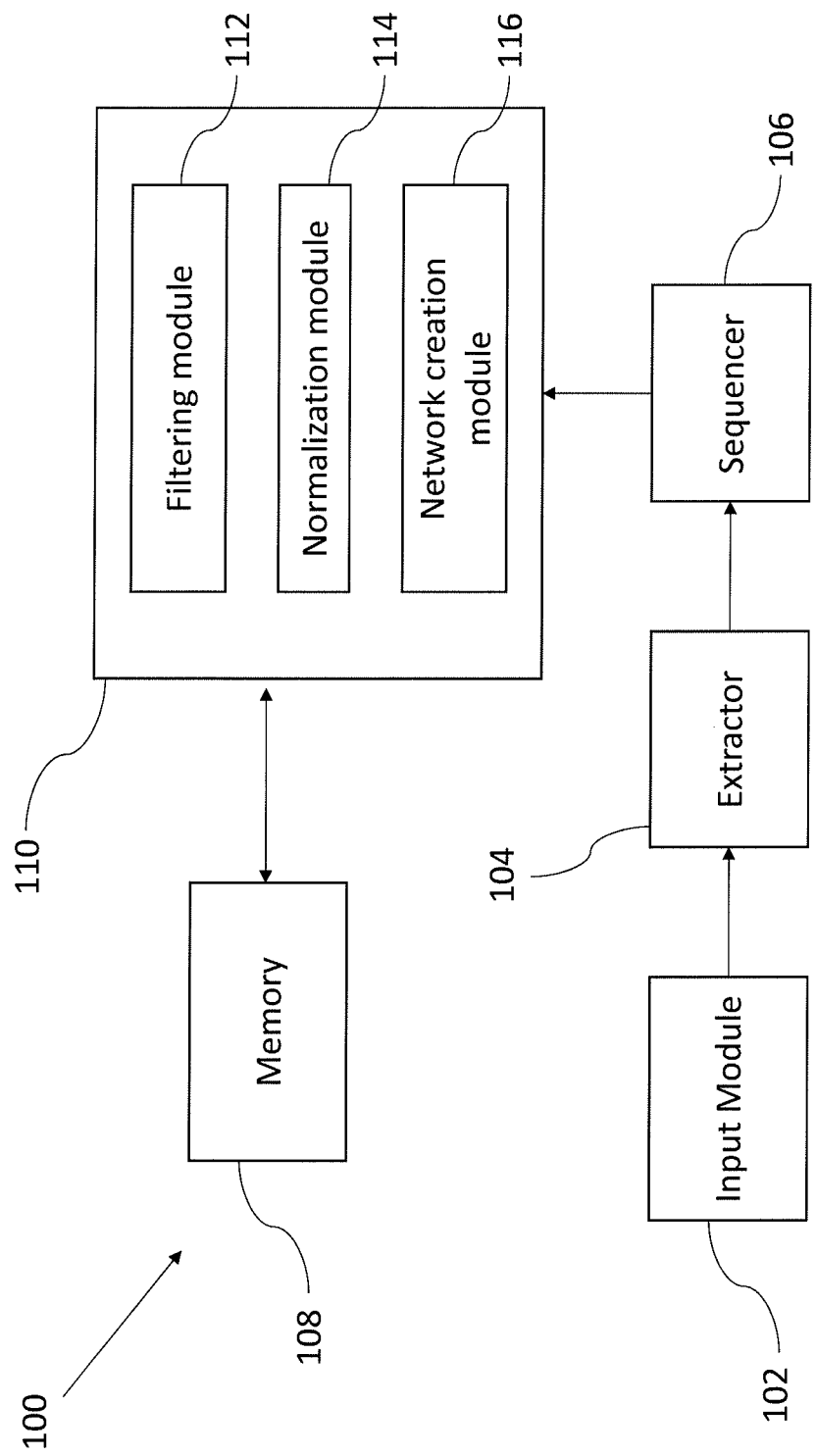
FIG. 1 illustrates a block diagram of a system for the identification of key driver organisms responsible for bringing changes in a microbial population according to an embodiment of the present disclosure.

Referring now to the drawings, and more particularly to FIG. 1, where similar reference characters denote corresponding features consistently throughout the figures, there are shown preferred embodiments and these embodiments are described in the context of the following exemplary system and/or method.

According to an embodiment of the disclosure, a system 100 for the identification of key driver responsible for bringing changes in a microbial population is shown in the block diagram of FIG. 1. The key driver is an organism or species which have a critical role in onset and progression of the disease. The system 100 is configured to compare a case-control study for the healthy and the diseased set of individuals. The microbial abundance matrix is available for both healthy and diseased states. The system 100 is configured to calculate the neighbor shift (NESH) index of candidate genera using a NetShift methodology and subsequently identify its statistical significance to be a key 'driver' of the disease.

According to an embodiment of the disclosure, the system 100 is primarily configured to receive human micro-biome samples from two different classes of human subjects, namely case and control. In another embodiment, the system 100 can also collect the micro-biome samples from any two different environments not restricted to human micro-biome only. Further in yet another embodiment, the system 100 can collect the micro-biome samples from a single environment at two or more different time-points.

According to an embodiment of the disclosure, the system 100 comprises an input module 102 or user interface 102, an extractor 104, a sequencer 106, a memory 108 and a processor 110 in communication with the memory 108 as shown in FIG. 1. The processor 110 configured to execute a plurality of algorithms stored in the memory 108. The processor 106 further includes a plurality of modules for performing various functions.

The input module 102 is configured to receive the sample from a first set of the individuals and a second set of individuals. The sample is generally collected from different part of human body from different environments such as lung, gut, skin etc. It should be appreciated that the first set may be from diseased (case) 'D' individuals and the second set is from the healthy (control) 'H' individuals. In another embodiment, the first set of individuals are in a reference state and the second set of individuals are in a perturbed state. The input module 102 may include a variety of software and hardware interfaces. In an example, the input module 102 can be referred as the user interface or input/output interface 102. The I/O interface user may allow the system 100 to interact with the user directly or through the client devices. The input module 102 can facilitate multiple communications within a wide variety of networks and protocol types, including wired networks, for example, LAN, cable, etc., and wireless networks, such as WLAN, cellular, or satellite. The input module 102 may include one or more ports for connecting a number of devices including assistive technology devices or adaptive products used by people with disability to one another or to another server.

The samples received from the first and the second set of individuals is utilized to extract DNA samples from them using the DNA extractor 104. Further, the DNA samples are then sequenced using the sequencer 106. The sequencing is performed using high-throughput sequencing techniques. The sequencing results in the generation of a plurality of DNA sequences. In an embodiment, the sequencer 106 subsequently, amplifies and sequences either full-length or specific variable regions of the bacterial 16S rRNA marker genes from the extracted microbial DNA. In another embodiment, the DNA samples can be amplified and sequenced to one or more phylogenetic marker genes other than (or in addition to) the 16S rRNA marker genes. A Whole Genome Shotgun (WGS) sequencing of the collected micro-biome is performed. In yet another embodiment, the sequencing is performed using approaches which involve either a fragment library, a mate-pair library, a paired-end library or a combination of the same.

The system 100 further includes the filtering module 112. The filtering module 112 is configured to filter the plurality of DNA sequences. The low quality sequences are removed using the filtering module 112. The filtering module 112 also clusters the similar sequences together. The filtering module 112 also configured to remove the non-essential DNA fragments. The output sample obtained from the filtering module 112 is used for the calculation of the NESH score.

According to an embodiment of the disclosure the system 100 is configured to create a 'microbial abundance profile' of the plurality of DNA sequences corresponding to the samples derived from the first set of individuals and the second set of individuals. The microbial abundance profile comprises of the abundance values of various individual 'taxonomic groups' present in the sequenced micro-biome sample. Thus, two matrices are created corresponding to the first and the second set of individuals respectively. The rows of the matrices represent various taxonomic groups (hereafter referred to as 'taxon/taxa/genera') and the columns represent the presence of taxon in the corresponding samples. The matrices cells for taxa absent in a sample is set to zero. The system 100 further configured to represent microbial organisms in each matrix as a plurality of nodes.

According to another embodiment of the disclosure, the microbial abundance profile can be generated using assignment based taxonomic classification (binning) approaches which involve comparing sequence and/or compositional level similarity of obtained micro-biome sequence data against existing reference sequence databases. In yet another embodiment, initially the sequenced DNA data corresponding to 16S rRNA marker genes (or other phylogenetic marker genes) is computationally analyzed and then the microbial abundance profile can be generated by segregating the DNA sequences into Operational Taxonomic Units (OTUs). This segregation may be based on clustering sequences based on their level of sequence level similarity. In yet another embodiment the sequenced DNA data corresponding to either phylogenetic marker genes or WGS sequence data are computationally analyzed and the microbial abundance profile is generated by segregating/clustering the DNA sequences based on compositional similarity.

The system 100 further comprises a normalization module 114 to normalize the matrices using a normalizing method. In an embodiment, the system 100 is using Cumulative Sum Scaling (CSS) procedure as the normalizing method. The use of any other normalizing method is well within the scope of this disclosure. The CSS procedure is explained as follows: Assume count matrix to be M (m,n), where m and n are number of taxa and samples respectively and $c_{ij}$ to be number of times $i^{th}$ taxa was observed in $j^{th}$ sample.

$l^{th}$ quantile of sample j is represented as $q^l_j$, which denotes that in sample j, l taxa have abundance counts less than $q^l_j$. Also, $$s^l_j = \sum_{i | c_{ij} \leq q^l_j} c_{ij}$$

which denotes the sum of counts for sample j upto the $l^{th}$ quantile. Normalized counts are defined as:

$$\widetilde{c_{ij}} = \frac{c_{ij}}{s^{\hat{l}}_j} N$$

where $\hat{l}$ is a specific value of l, which is determined in a data-driven manner explained in the Step 2b and N is a scaling factor, which is same for all the samples. $\hat{l}$ is determined dynamically based on the data provided. To achieve this, the median of $l^{th}$ quantile across samples i.e. $\bar{q}^l = med_j\{^l_j\}$ and median absolute deviation i.e. $d_l = med_j|q_j^l - \bar{q}^l|$ are calculated. Choose $\hat{l}$ to the smallest l that satisfies $d^{l+1} - d^l \geq 0.1 d^l$.

In another embodiment of the disclosure, the matrices are normalized using taxonomic abundance counts. The taxonomic abundance counts can use at least one of a total taxonomic abundance for that particular sample, mean/median taxonomic abundance for that particular sample, or abundance of any reference taxa.

The system 100 further configured to generate the microbial association network for the first set and the second set of individuals for each of the matrices using a network creation module 116. In an embodiment the microbial association network is generated as follows: Initially, for matrix for the healthy state of individuals ($M_H$), the array of each constituent taxa ($T_1 \ldots T_n$) is extracted. After that, Pearson correlation, Spearman correlation, Bray-Curtis dissimilarity and Kullback-Leibler dissimilarity are calculated for taxon arrays of any particular pair of taxa. Followed by randomizing the taxa arrays and again calculating the aforementioned correlation/dissimilarity indices to generate a distribution of all four of these measures. In the next step, based on the distribution obtained in the previous step, the p-value of the original index is calculated. Only those edges are retained, which have an associated p-value less than 0.05. Then the edge between any two taxa is considered to be significant only if three out of four indices agree upon it. And finally, all edges quantified in the previous step are listed to get the microbial association network $N_H$. The similar steps are repeated for matrix for the diseased state of individuals ($M_D$) for diseased set of individuals and the microbial association network $N_D$ is obtained.

The system 100 further configured to compute the Jaccard node index ($J_N$) and Jaccard edge index ($J_E$) between the microbial association network of first set and the microbial association network of the second set. In an embodiment, the following formula can be used for the calculation:

$$\text{Jaccard node index} = \frac{A_N \cap B_N}{A_N \cup B_N}$$

$$\text{Jaccard edge index} = \frac{A_E \cap B_E}{A_E \cup B_E}$$

Where, $A_N$ and $B_N$ is the total nodes, $A_E$ and $B_E$ are the total edges in network A and B respectively. A represents to the first set of individuals and B represents to the second set of individuals.

Figure 2:
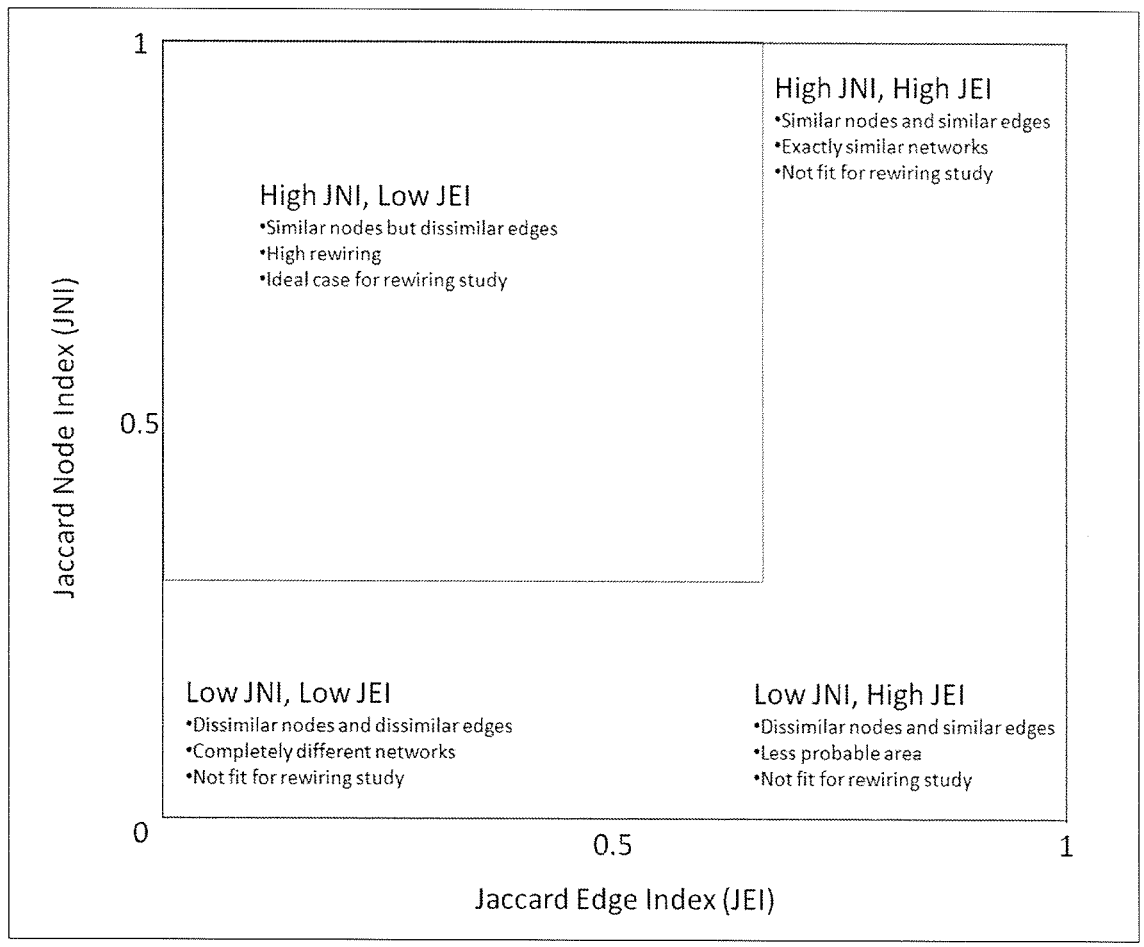
FIG. 2 shows a graphical representation of Jaccard node index and Jaccard edge index according to an embodiment of the present disclosure.

According to another embodiment of the disclosure, the processor 110 is configured to identify the nodes which have the Jaccard node index is higher than a first predefined value and the Jaccard edge index is lower than a second predefined value. In an embodiment, the first predefined value is any value between 0.6 and 1 and the second predefined value is any value between 0 and 0.6. It should be appreciated that the user may select any other range of for the first predefined value and the second predefined value. This confirms a high rewiring between the two sets with minimal addition or removal of another node Based on the above mentioned criteria a plot is created as shown in FIG. 2. The X-axis represents the Jaccard edge index and the Y-axis represents the Jaccard node index. A network is expected to be rewired, if the Jaccard node index is high (most of the nodes are similar) while the Jaccard edge index is low (most of the edges is different). A point having high $J_N$ and low $J_E$ (the shaded area of the plot in FIG. 2) is expected to be highly rewired and can be counted to be an ideal case to apply the NetShift algorithm.

According to an embodiment of the disclosure, the system 100 is further configured to computer the scaled change in betweenness for each of the nodes in the microbial association network of second set of individuals with respect to the microbial association network of the first set of individuals. Following formula is used for the scaled betweenness ($B_{scaled}$) for each of the nodes in both of the networks using the formula:

$$B_{scaled} = \frac{B_{calculated} - B_{min}}{B_{max} - B_{min}}$$

Where, $B_{calculated}$, $B_{min}$ and $B_{max}$ correspond to the calculated, min and max betweenness values. Further, scaled change in betweenness ($\Delta B^n$) is computed for each of the common nodes second set of individuals with respect to the microbial association network of the first set of individuals.

$$\Delta B^n = B_{scaled}{}^n{}_D - B_{scaled}{}^n{}_H$$

Where, $B_{scaled}{}^n{}_D$ and $B_{scaled}{}^n{}_H$ correspond to the scaled betweenness of node 'n' in diseased and healthy state respectively.

The system 100 is further configured to calculate the Neighbor shift (NESH) score for the microbial association network of the second set with respect to the microbial association network of the first set using a predefined formula. In an embodiment the formula used is:

$$NESH = \left(\frac{f^A_{n_i} \cap f^B_{n_i}}{f^A_{n_i} \cup f^B_{n_i}}\right) - \left(\frac{f^B_{n_i} - f^A_{n_i}}{10} + \frac{f^B_{n_i} - f^A_{n_i}}{f^B_{n_i} \cup f^A_{n_i}}\right)$$

Where $n_i$ is the 'i'th node in the union of compared networks A and B corresponding to healthy and diseased states respectively. $f^A_{n_i}$ and $f^B_{n_i}$ are the first neighbors of $n_i$ in the networks A and B respectively. The score can be broken down into three components: X, Y and Z:

Where, $$X = \left(\frac{f_{n_i}^A \cap f_{n_i}^B}{f_{n_i}^A \cup f_{n_i}^B}\right); Y = \frac{f_{n_i}^B - f_{n_i}^A}{10}; Z = \frac{f_{n_i}^B - f_{n_i}^A}{f_{n_i}^B \cup f_{n_i}^A}$$

Such that, NESH=X−(Y+Z)

The component X provides a measure of the extent of neighborhood similarity irrespective of the direction of change, while component Y and Z penalizes X over exclusive enrichment in the set of first neighbors corresponding to the disease set over the healthy. The component Y specifically penalizes for cases where the control set has no neighbors and also helps to distinguish differential set contents in the said scenario. Component Z on the other hand penalizes X for exclusive new first neighbors over the union of all first neighbors in both disease and healthy combined. Thus more negative the NESH score, higher the amount of neighborhood shift is accounted for a node.

Further, the system 100 is configured to calculating the statistical significance (P value) for the NESH score for each of the nodes. Let, the number of elements in set A=$N_A$, number of elements in set B=$N_B$, and number of common elements between the sets=$N_C$. Thus, the formula of NESH can be re-written as follows:—

$$NESH = \frac{N_C}{N_A + N_B - N_C} - \frac{N_A - N_C}{10} - \frac{N_A - N_C}{N_A + N_B - N_C}$$

Considering the number of elements in sets A and B to be constant, number of common elements between A and B i.e. $N_C$ can be varied from 0 to min($N_A$,$N_B$). In that case, NESH can be considered as a function of $N_C$. Although, originally NESH was defined only for integer values of $N_C$, nonetheless it may well be extended as a continuous function for all real values of $N_C \in [0, \min(N_A, N_B)]$. Differentiation of NESH function with respect to $N_C$ yields the following:—

$$\frac{d(NESH)}{dN_C} = \frac{N_A + 2N_B}{(N_A + N_B - N_C)^2} + \frac{1}{10}$$

Above expression of $$\frac{d(NESH)}{dN_C}$$

is positive for all values of $N_C \in [0, \min(N_A, N_B)]$. This signifies that NESH is an increasing function of $N_C$ and therefore, likelihood of getting any NESH≤$NESH_{obs}$ at random is same as that of $N_C \leq N_{C\,obs}$. Further, for any particular value of $N_C$, number of all possible combinations is:

$$\binom{N_A + N_B - N_C}{N_C}$$

Therefore, probability of getting an NESH value less than or equal to an observed NESH value can be written as:

$$p = \frac{\sum_{x=0}^{N_{Cobs.}} \binom{N_A + N_B - x}{x}}{\sum_{x=0}^{\min(N_A, N_B)} \binom{N_A + N_B - x}{x}}$$

Further, the system 100 is configured to check the criticality of the calculated NESH score. A node will be identified as the key driver if the statistical significance value of its neighbor shift score is less than a third predefined value and the scaled change in betweenness is positive. In an embodiment, the nodes with a p-value less than or equal to 0.1 and a positive delta betweenness (AB) are identified as 'critical' or 'driver' genera/nodes. It should be appreciated that the user can also define any other stringent p-value cutoff depending on their requirements.

According to another embodiment of the disclosure, the criticality for an $n^{th}$ 'driver' can also be calculated using the following equation:

$$NESH_{critical} = NESH*(1-p)*(1+\Delta B^n)$$

According to another embodiment of the disclosure, the system 100 is also configured to calculate a cumulative critical score for the network pair. The cumulative critical score is calculated by summing up the individual critical scores for the 'driver' nodes/genera as follows:

Cumulative $NESH\,critical = \sum_{i=1}^{n} NESH_{critical}$

Where, 'n' represents the total identified 'driver' nodes/genera.

Figure 3A:
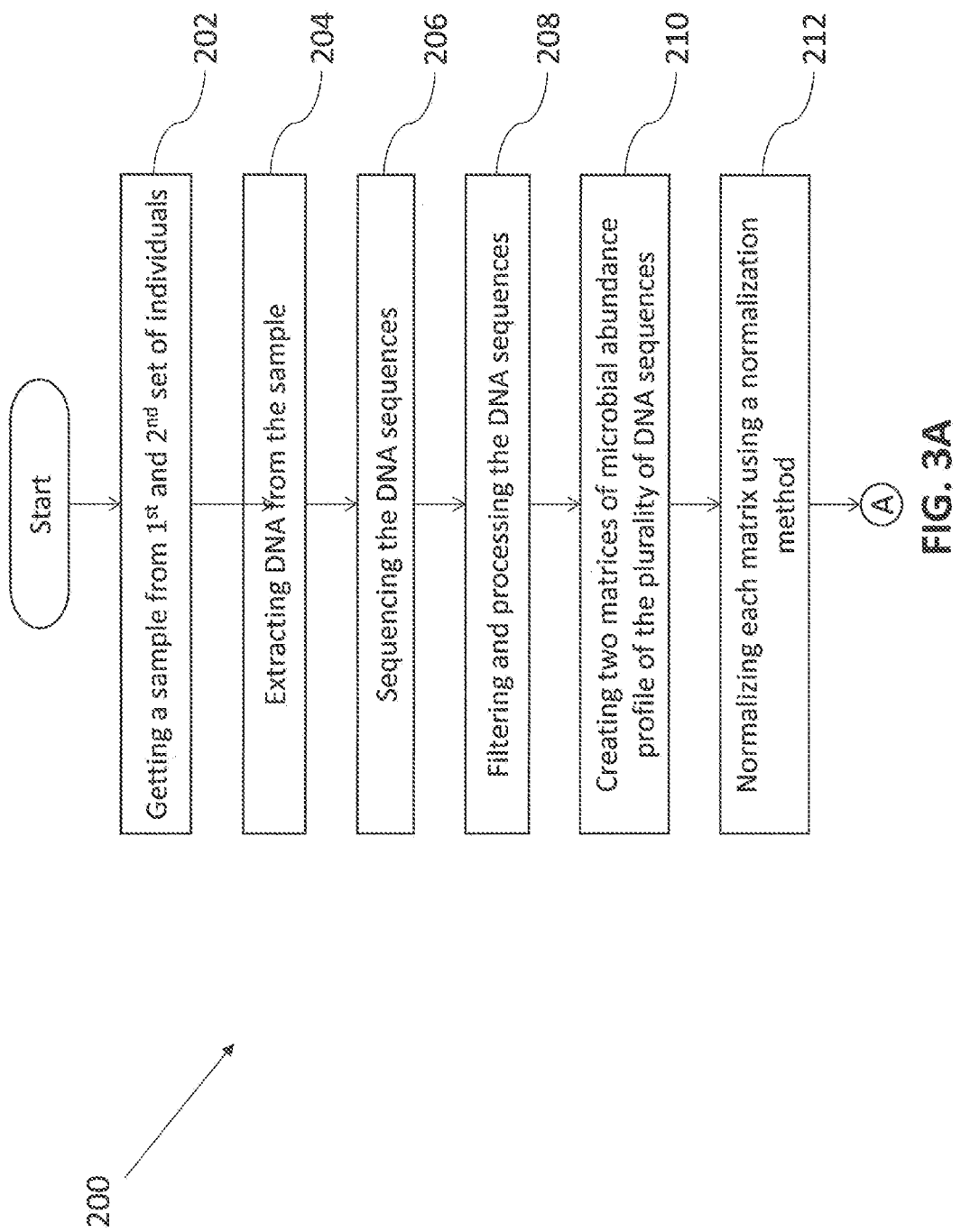
Figure 3B:
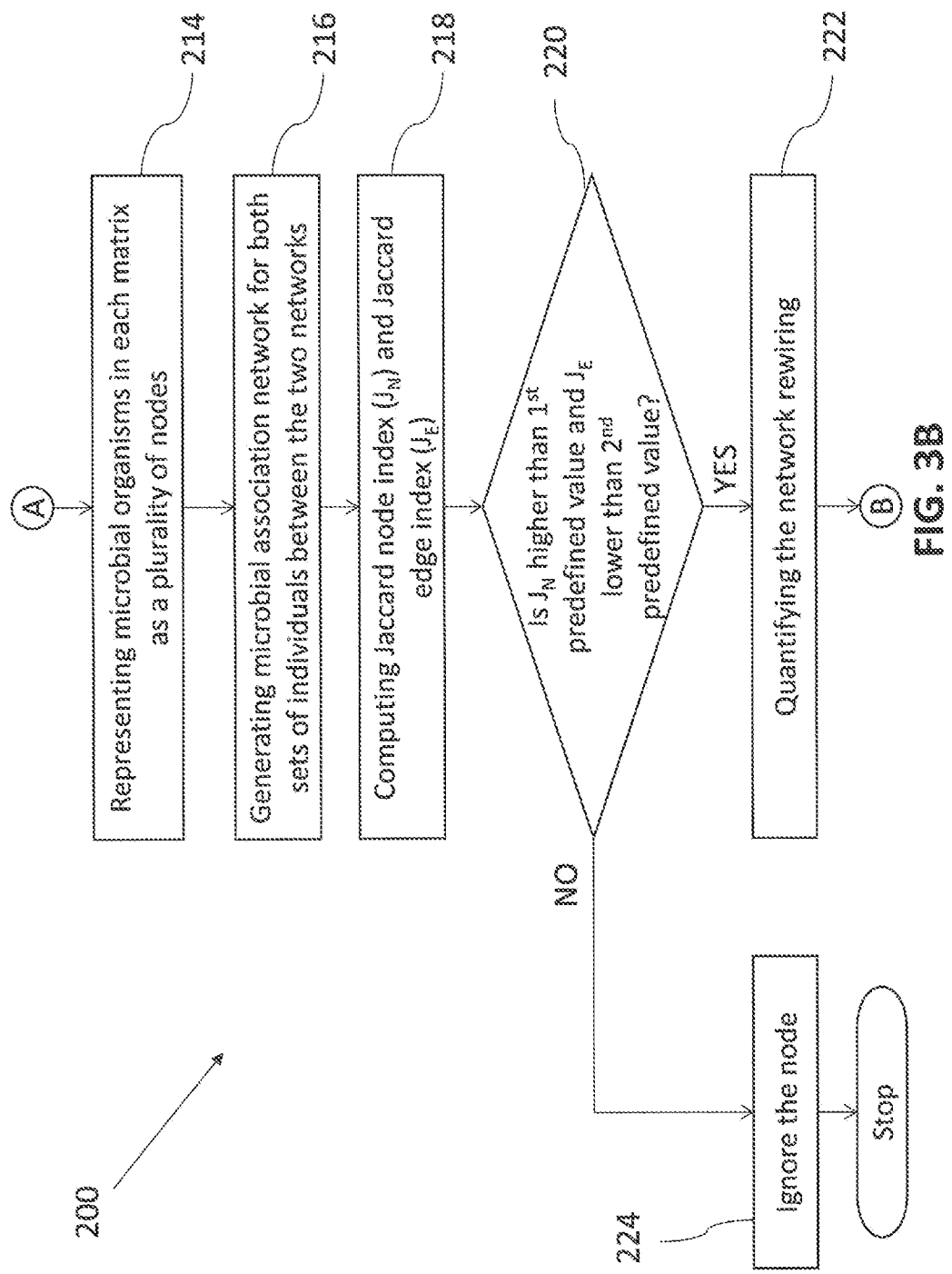

In operation, a flowchart 200 illustrates the steps involved for identification of key driver responsible for bringing a change in a microbial population as shown in FIGS. 3A-3C according to an embodiment of the disclosure. Initially at step 202, a sample from a first set of individuals and a second set of individuals is acquired using an input module 102. In an embodiment the first set of individuals are in diseased state while the second set of individuals are in healthy state. Further, the healthy state can be referred as the reference state and the diseased state can be referred as the perturbed state. At step 204, DNA samples are extracted from the samples from the first and the second set of individuals. At the next step 206, each of the DNA samples are sequenced using a throughput sequencer 106 to generate a plurality of DNA sequences. Normally, the DNA sequences obtained in the previous step may contain a lot of reads of low quality, therefore at the next step 208, the plurality of DNA sequences are filtered and processed for removing the low quality DNA sequences and non-essential DNA fragments.

At step 210, two matrices of microbial abundance profile of the plurality of DNA sequences are created corresponding to the first set of individuals and the second set of individuals. Each matrix of microbial abundance profile includes abundances of microbial organisms corresponding to each members belonging to the microbial population. In the next step 212, each of the matrix is normalized using a normalization method. In an embodiment cumulative sum scaling method have been used for normalization. After normalization, at step 214, the microbial organisms in each matrix is represented as the plurality of node. In step 216, a microbial association network is generated for the first set of individuals and the second set of individuals using the normalized matrices between the two networks.

At step 218, Jaccard node index and Jaccard edge index are computed between the microbial association network of first set and the microbial association network of the second set. At step 220, it is checked that whether if the Jaccard node index is higher than a first predefined value and Jaccard edge index is lower than a second predefined value. If YES then at step 222, the network rewiring is quantified based on the identified Jaccard node index and Jaccard edge index. If NO then at step 224, the network pair is ignored for further analysis. In an embodiment, the first predefined value is between 0.6 and 1 and the second predefined value is between zero and 0.6. It should be appreciated that the user may select any other range of for the first predefined value and the second predefined value.

At step 226, a scaled change in betweenness is computed for each of the nodes in the microbial association network of the second (perturbed) set with respect to the microbial association network of the first set. At step 228 a neighbor shift score is calculated for each of the nodes in the microbial association network of the second set with respect to the microbial association network of the first set using a predefined formula. In the next step 230, a statistical significance value for the neighbor shift score is calculated for each of the nodes. At step 232 it is checked for any particular node that whether the statistical significance value of its neighbor shift score is less than a third predefined value and the scaled change in betweenness is positive. Is YES then at step 234, it is identified that the particular node is the key driver organism. Else, the node is not the key driver organism. In the embodiment, it can also be concluded that the key driver organism is responsible for bringing any changes in disease of the individual.

Figure 4:
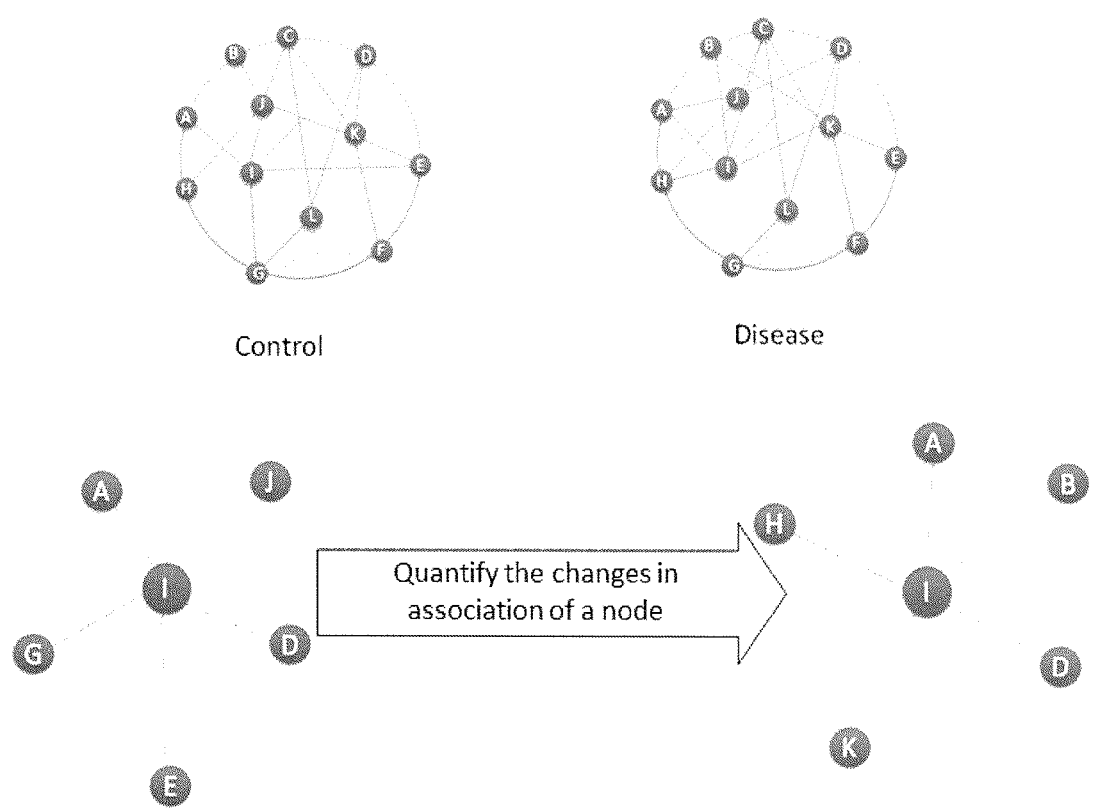
FIG. 4 illustrates a rationale for NESH scoring according to an embodiment of the disclosure.

According to an embodiment of the invention, the rationale for NESH scoring can be explained with the help of following example as shown in FIG. 4. As shown in the FIG. 4, two representative networks 'Control' (say A) and 'Disease' (say B) are shown having 12 nodes rewired differently in either network. The NetShift methodology aims to identify 'driver' nodes involved in the rewiring event which is observed between the healthy and diseased state. One of the steps employed in the NetShift methodology involves calculation of a NESH score to quantify the changes in association of a node between a healthy (control) and diseased state. For a representative node I which had neighbors A, G, E, D and J in 'Control' while A, B, H, D and K in 'Disease' network although the degree for node T is same in both network, it's associations are different. The NESH score provides a way to quantify these changes in association and is calculated as:

$$NESH = \left(\frac{f_{n_i}^A \cap f_{n_i}^B}{f_{n_i}^A \cup f_{n_i}^B}\right) - \left(\frac{f_{n_i}^B - f_{n_i}^A}{10} + \frac{f_{n_i}^B - f_{n_i}^A}{f_{n_i}^B \cup f_{n_i}^A}\right)$$

Where $n_i$ is the 'i'th node in the union of compared networks A and B corresponding to healthy and diseased states respectively (consisting of a total of N nodes). $f_{ni}^A$ and $f_{ni}^B$ are the first neighbors of $n_i$ in the networks A and B respectively.

Thus, this step is necessarily a quantification of a directional change between two sets. Scores commonly used to quantify such scenarios include Jaccard index and Ochiai index as described below.

$$\text{Jaccard index} = \sum_{i=1}^{N}\left(\frac{A \cap B}{A \cup B}\right)$$

$$\text{Ochiai} = \frac{n(A \cap B)}{\sqrt{n(A) \cdot n(B)}}$$

Where, A and B corresponds to the two compared sets. The NESH score was evaluated with the above two scores against various biologically occurring scenarios and the results are summarized in the Table as shown in FIG. 5. As evident from the table, in all the six scenarios, the NESH score successfully discriminates the changes between the disease and healthy states. In only one scenario, all the three indices perform equally. It is interesting to note in the fourth scenario, that although the Jaccard index assigns a variable score as a whole, it still assign similar score to multiple sub-scenarios. Further, in the same case, the Ochiai index although could assign a variable score for the sub-scenarios, it assigned a greater similarity score for the undesired scenario. NESH score on the other hand scores all the scenarios correctly (N.B: More negative NESH score indicates a higher change).

The present disclosure provides applicability to various industries. The system and method has immense applicability for meta-genomics researchers as well as researchers working in diverse areas of biological research, ranging from medical microbiology, to industrial and environmental biotechnology. In addition to that, the present disclosure can also be useful for health care professionals, pharmaceutical companies, researchers working in understanding disease pathogenesis, environmental biologists/Organizations involved in bio-remediation, microbial Ecologists, professionals working in industrial microbiology etc.

Test Case Studies:

Further, the NetShift methodology can be tested on simulated networks as follows. In the first step, to evaluate rewiring, NESH score and total 'driver' nodes, random networks were created with a fixed set of 30 nodes but a varying number of edges. In a fully connected network of 30 nodes, it is possible to have 435 edges. To generate networks with varying amount of rewiring, 8 sets were chosen corresponding to 125, 150, 175, 200, 250, 300, 350 and 400 edges respectively with the fixed set of 30 nodes. Each set consisted of 100 random networks with the selected set of nodes and edges.

Figure 6:
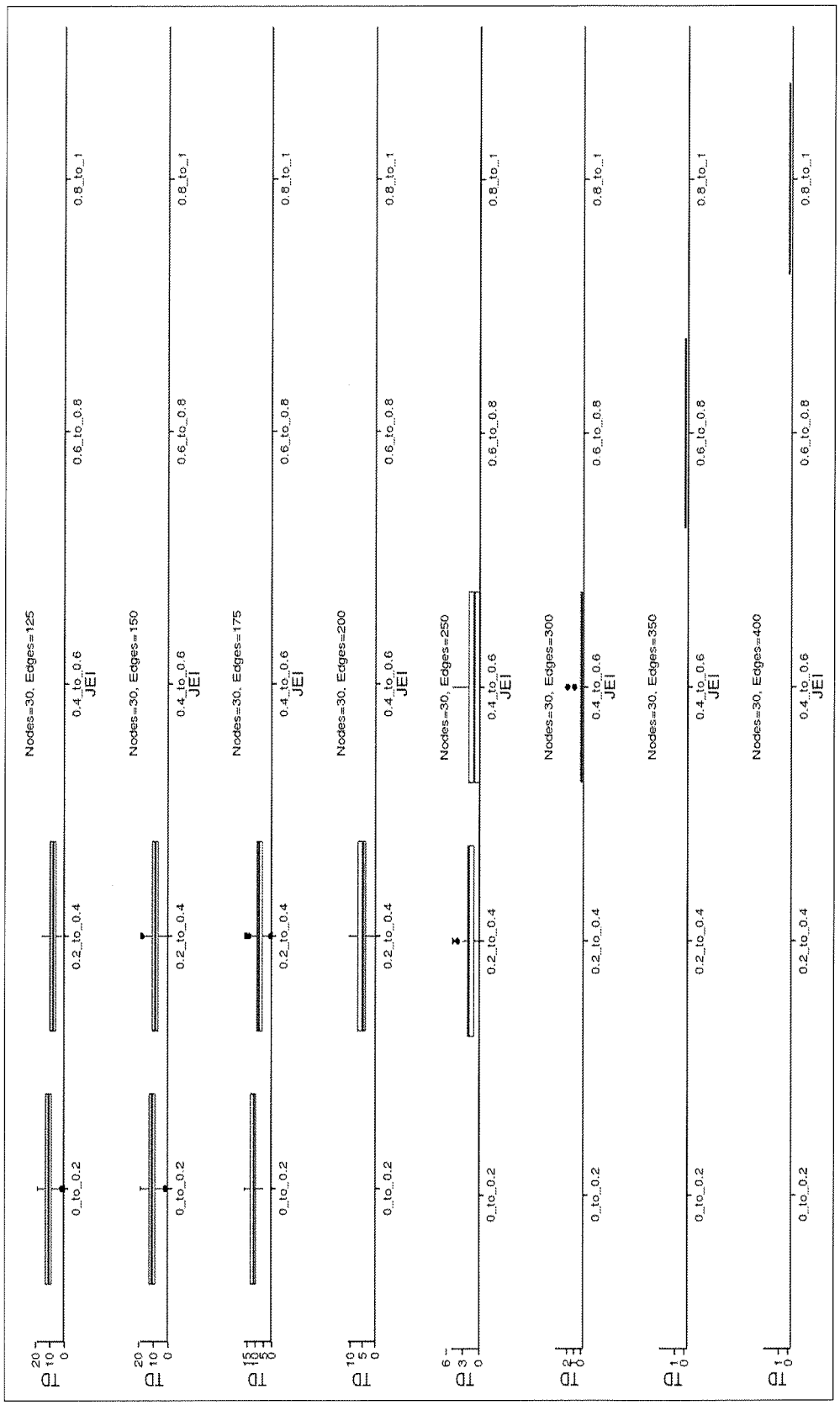
FIG. 6 shows a plot of total identified 'drivers' ($N_D$) vs. Jaccard edge index ($J_{EI}$) for each of the 8 sets according to an embodiment of the present disclosure.

In the next step, the all vs. all network similarities were calculated in term of Jaccard edge index $J_E$ (Jaccard node index being 1 for all cases as the total nodes are exactly similar for all the networks). Lower $J_E$, in this case signifies a higher rewiring. Further the cumulative NESH score was calculated and total critical nodes for each compared pair. The FIG. 6 shows a plot of total identified 'drivers' (ND) vs. Jaccard edge index ($J_E$) for each of the 8 sets. The relation between the $J_E$ and total edges can be easily observed for simulated exercise. Keeping nodes same, an increase in number of edges increases the $J_E$ due to the saturation in the degree of freedom for edge creation. A lower number of edges give the nodes a higher chance to rewire and subsequently give rise to higher number of 'drivers'. Additionally, it is interesting to note that for sets with edges ranging for 125 to 175 (28% to 40% of edges when fully connected), a significantly higher stretch in the range of JEI is observed (0.1 to 0.4) with a fairly similar number of average nodes as 'drivers' (~10). This indicates that lower $J_E$ values are most suited for NetShift methodology due to a higher amount of rewiring. It can be noted that $J_E$ is non-directional while the critical NESH depends on the reference (healthy) and the case (disease) network. Hence a $J_E$ from network 'A'→μV and 'B'→'A' will be same while the cumulative NESH score as well as the total 'driver' nodes will be different.

Further method can be tested with real world data sets as follows: For doing same previously studied lung microbiome datasets pertaining to HIV infection were chosen and analyzed as explained in the research paper by "Lozupone, C., Cota-Gomez, A., Palmer, B. E., Linderman, D. J., Charlson, E. S., Sodergren, E., et al. (2013) in Widespread Colonization of the Lung by Tropheryma whipplei in HIV Infection. Am J Respir Crit Care Med 187, 1110-1117. doi:10.1164/rccm.201211-2145OC." The study corresponded to healthy and HIV infected individuals from several geographies out of which it was chosen to analyze three as they had a decent representative samples belonging to both HIV− and HIV+ group as shown in the table below:

| Sample name in original study | Abbreviated sample name | HIV− | HIV+ |
|---|---|---|---|
| LHMP_Colorado | Colorado [C] | 35 | 20 |
| LHMP Indiana | Indiana [I] | 22 | 29 |
| LHMP_Upenn | Penn [P] | 24 | 23 |

The OTU abundance table for the HIV datasets was extracted from the main 'biom' files using the biom-format project. The individual taxonomic abundance profiles were obtained from the supplementary material from the prior art. Abundance values of OTUs belonging to the same genus were cumulated to obtain genus level abundance tables for each study. CSS normalization was used to scale the taxonomic abundance matrices for each study using the metagenomeSeq package. The CSS normalization was performed as explained in the reference paper by "Paulson, J. N., Stine, O. C., Bravo, H. C., and Pop, M. (2013) in Differential abundance analysis for microbial marker-gene surveys. Nat. Methods 10, 1200-1202. doi:10.1038/nmeth.2658." The metagenomeSeq package were used from the research paper by "Faust, K., Sathirapongsasuti, J. F., Izard, J., Segata, N., Gevers, D., Raes, J., et al. (2012) in Microbial Co-occurrence Relationships in the Human Microbiome. PLoS Comput Biol 8, e1002606. doi:10.1371/journal.pcbi.1002606." Microbial co-occurrence networks were generated using an ensemble scoring methodology using four measures namely Pearson, Spearman, Bray-Curtis and Kullback-Leibler (KLD). The above method relies on a consensus of several different mathematical scoring schemes to ascertain the presence of any edge. CoNet plugin was used in Cytoscape to create the individual networks pertaining to the three datasets. The CoNet plugin was used from the research paper by "Faust, K., Sathirapongsasuti, J. F., Izard, J., Segata, N., Gevers, D., Raes, J., et al. (2012) in Microbial Co-occurrence Relationships in the Human Microbiome. PLoS Comput Biol 8, e1002606. doi:10.1371/journal.pcbi.1002606." For each of the three datasets, one control (HIV−) and one diseased (HIV+) state network was generated.

NetShift methodology was used to study the rewiring using the reference plot which ascertained the feasibility of applying the NetShift methodology. The NetShift tool was used to identify the 'driver' taxa for the three datasets corresponding to HIV infection as shown in the table below. The table includes a supplementary data collected from three states 1 (Indiana), 2 (Colorado) and 3 (Penn). This data was taken from various research papers for the plurality of nodes. The Indiana [I] and Colorado [C] dataset were observed to have several 'driver' nodes while NetShift method could not find any 'driver' nodes for the Penn [P] dataset. The identified 'driver' genera were searched for literature evidence and the results are summarized in the table 1 below. The literature evidences clearly support our identified 'driver' taxa using the NetShift methodology.

TABLE 1

Identification of driver nodes in Indiana, Colorado and Penn states

| Abbreviated sample name | Jaccard Node Index | Jaccard Edge Index | Total critical nodes | Cumulative NESH score | Average Viral Load |
|---|---|---|---|---|---|
| Indiana [I] | 1 | 0.18 | 13 | −12.36 | 153791.17 |
| Colorado [C] | 1 | 0.39 | 4 | −5.87 | 58245 |
| Penn [P] | 0.97 | 0.44 | 0 | 0 | 9686.83 |

Further, Supplementary data taken for Indiana [I], Colorado [C] and Penn [P] is shown in Table 2, Table 3 and Table 4 below respectively. The Tables show various nodes along with their tag, NESH score, p-value, delB and critical score:

TABLE 2

Supplementary data for Indiana

| Node | tag | NESH | p-value | delB | critical_score |
|---|---|---|---|---|---|
| g_Ralstonia | CRITICAL | −1.8 | 0.1 | 0.361693 | −2.205942397 |
| g_TG5 | CRITICAL | −1.167 | 0.001013 | 0.217383 | −1.418841239 |
| g_Peptostreptococcus | CRITICAL | −1.163 | 0.113232 | 0.282289 | −1.322618418 |
| g_Delftia | CRITICAL | −1.1 | 0.07971 | 0.180599 | −1.195142166 |
| g_Porphyromonas | CRITICAL | −0.936 | 0.118121 | 0.094732 | −0.903986159 |
| g_Moryella | CRITICAL | −0.787 | 0.105691 | 0.167089 | −0.821943982 |
| g_Bulleidia | CRITICAL | −0.964 | 0.183784 | 0.026981 | −0.80775719 |
| g_Staphylococcus | CRITICAL | −0.714 | 0.067043 | 0.120503 | −0.746701244 |
| g_Lactobacillus | CRITICAL | −0.705 | 0.113232 | 0.169308 | −0.731290451 |
| g_Eubacterium | CRITICAL | −0.688 | 0.033374 | 0.023507 | −0.680177375 |
| g_Catonella | CRITICAL | −0.625 | 0.105848 | 0.159583 | −0.648027423 |
| g_Selenomonas | CRITICAL | −0.545 | 0.050216 | 0.097246 | −0.568443836 |
| g_Streptococcus | CRITICAL | −0.3 | 0.064056 | 0.107717 | −0.311028369 |
| g_Atopobium | NON-CRITICAL | −0.643 | 0.006191 | −0.95965 | 0 |
| g_Haemophilus | NON-CRITICAL | −0.438 | 0.009041 | −0.48971 | 0 |
| g_Rothia | NON-CRITICAL | −0.418 | 0.011292 | −0.049 | 0 |
| g_Flavobacterium | NON-CRITICAL | −0.382 | 0.021277 | −0.02568 | 0 |
| g_Gemella | NON-CRITICAL | −0.256 | 0.026573 | −0.1989 | 0 |
| g_Treponema | NON-CRITICAL | −1.2 | 0.029611 | −0.09337 | 0 |

TABLE 2-continued

Supplementary data for Indiana

| Node | tag | NESH | p-value | delB | critical_score |
| --- | --- | --- | --- | --- | --- |
| g__Actinomyces | NON-CRITICAL | −0.611 | 0.057666 | −0.70993 | 0 |
| g__Capnocytophaga | NON-CRITICAL | −0.371 | 0.079259 | −0.2336 | 0 |
| g__Granulicatella | NON-CRITICAL | −0.152 | 0.087773 | −0.48953 | 0 |
| g__Tropheryma | NON-CRITICAL | −0.3 | 0.106796 | −0.14539 | 0 |
| g__Filifactor | NON-CRITICAL | −1.689 | 0.111111 | 0 | 0 |
| g__Propionibacterium | NON-CRITICAL | −0.5 | 0.152528 | −0.10547 | 0 |
| g__Campylobacter | NON-CRITICAL | −0.152 | 0.202787 | −0.85748 | 0 |
| g__Fusobacterium | NON-CRITICAL | −1.182 | 0.236405 | 0.08697 | 0 |
| g__Mogibacterium | NON-CRITICAL | −0.14 | 0.270681 | −0.78167 | 0 |
| g__Prevotella | NON-CRITICAL | −0.252 | 0.283817 | −0.81578 | 0 |
| g__Neisseria | NON-CRITICAL | −0.3 | 0.319714 | 0.060446 | 0 |
| g__Abiotrophia | NON-CRITICAL | −0.367 | 0.333333 | −0.03158 | 0 |
| g__Dialister | NON-CRITICAL | −0.6 | 0.415502 | 0.094045 | 0 |
| g__Veillonella | NON-CRITICAL | −0.295 | 0.416796 | 0.55382 | 0 |
| g__Oribacterium | NON-CRITICAL | 0.022 | 0.531216 | 0.031967 | 0 |
| g__Mycoplasma | NON-CRITICAL | −1.7 | 1 | 0.020619 | 0 |

TABLE 3

Supplementary data for Colorado

| Node | tag | NESH | p-value | delB | critical_score |
| --- | --- | --- | --- | --- | --- |
| g__Tropheryma | CRITICAL | −1.643 | 0.023328 | 0.152341 | −1.84897 |
| g__Peptostreptococcus | CRITICAL | −1.1 | 0.192017 | 0.978604 | −1.75855 |
| g__Moryella | CRITICAL | −1.133 | 0.14341 | 0.541078 | −1.49608 |
| g__Neisseria | CRITICAL | −0.8 | 0.076923 | 0.03306 | −0.76288 |
| g__Leptotrichia | NON-CRITICAL | −0.4 | 0.006198 | −0.62746 | 0 |
| g__Alicyclobacillus | NON-CRITICAL | −0.6 | 0.011852 | −0.72143 | 0 |
| g__Acinetobacter | NON-CRITICAL | −1.947 | 0.074519 | −0.14303 | 0 |
| g__Methyloversatilis | NON-CRITICAL | −0.733 | 0.11236 | −0.14903 | 0 |
| g__Actinobacillus | NON-CRITICAL | −0.1 | 0.130435 | −0.08253 | 0 |
| g__Catonella | NON-CRITICAL | −0.089 | 0.230027 | −0.69621 | 0 |
| g__Klebsiella | NON-CRITICAL | −0.433 | 0.333333 | −0.00745 | 0 |
| g__Morganella | NON-CRITICAL | −0.433 | 0.333333 | −0.04122 | 0 |
| g__Porphyromonas | NON-CRITICAL | −0.257 | 0.464219 | −0.0737 | 0 |
| g__Capnocytophaga | NON-CRITICAL | −1.143 | 0.464219 | 0.318245 | 0 |
| g__Staphylococcus | NON-CRITICAL | −0.7 | 0.5 | −0.16314 | 0 |
| g__Bulleidia | NON-CRITICAL | −0.62 | 0.544159 | −0.50721 | 0 |
| g__Dialister | NON-CRITICAL | −1.076 | 0.594377 | 0.091081 | 0 |
| g__Blautia | NON-CRITICAL | −0.925 | 0.661417 | 0.0133 | 0 |
| g__Treponema | NON-CRITICAL | −0.065 | 0.748139 | 0.017118 | 0 |
| g__Selenomonas | NON-CRITICAL | −0.752 | 0.791047 | −0.2156 | 0 |
| g__Atopobium | NON-CRITICAL | −0.713 | 0.808986 | −0.48188 | 0 |
| g__Granulicatella | NON-CRITICAL | −0.022 | 0.828433 | −0.07004 | 0 |
| g__Gemella | NON-CRITICAL | −0.096 | 0.903247 | 0.073191 | 0 |
| g__Haemophilus | NON-CRITICAL | −0.589 | 0.924952 | 0.832519 | 0 |
| g__Rothia | NON-CRITICAL | 0.229 | 0.956522 | −0.19108 | 0 |
| g__Streptococcus | NON-CRITICAL | −0.052 | 0.957792 | −0.09215 | 0 |
| g__Veillonella | NON-CRITICAL | −0.1 | 0.994903 | 0.009765 | 0 |
| g__Fusobacterium | NON-CRITICAL | 0.277 | 0.999834 | −0.55359 | 0 |
| g__Campylobacter | NON-CRITICAL | 0.142 | 0.999869 | 0.127286 | 0 |
| g__Prevotella | NON-CRITICAL | 0.2 | 0.99999 | 0.335569 | 0 |
| g__Propionibacterium | NON-CRITICAL | −1.256 | 1 | 0.135581 | 0 |
| g__Actinomyces | NON-CRITICAL | −0.306 | 1 | 0.140661 | 0 |

TABLE 4

Supplementary data for Penn

| Node | tag | NSI | p-value | delB | critical_score |
| --- | --- | --- | --- | --- | --- |
| g__Treponema | NON-CRITICAL | −1.333 | 0.001013 | −0.2528 | 0 |
| g__Dialister | NON-CRITICAL | −2.057 | 0.0125 | −0.09487 | 0 |
| g__Filifactor | NON-CRITICAL | −0.971 | 0.047619 | −0.09145 | 0 |
| g__Catonella | NON-CRITICAL | −1.133 | 0.14341 | −0.01046 | 0 |
| g__Capnocytophaga | NON-CRITICAL | −0.556 | 0.148339 | −0.02626 | 0 |
| g__Mycoplasma | NON-CRITICAL | −1.212 | 0.257143 | 0.036177 | 0 |
| g__Selenomonas | NON-CRITICAL | −1.618 | 0.266439 | 0.126711 | 0 |
| g__Leptotrichia | NON-CRITICAL | −1.267 | 0.280237 | 0.162808 | 0 |
| g__Tannerella | NON-CRITICAL | −0.4 | 0.461538 | −0.15877 | 0 |

TABLE 4-continued

Supplementary data for Penn

| Node | tag | NSI | p-value | delB | critical_score |
|---|---|---|---|---|---|
| g__Mogibacterium | NON-CRITICAL | 0.027 | 0.470171 | −0.17221 | 0 |
| g__Alicyclobacillus | NON-CRITICAL | −2.323 | 0.631811 | 0.973328 | 0 |
| g__Streptococcus | NON-CRITICAL | −0.757 | 0.672114 | −0.0267 | 0 |
| g__Eubacterium | NON-CRITICAL | −0.2 | 0.707595 | −0.01371 | 0 |
| g__Neisseria | NON-CRITICAL | −0.05 | 0.710109 | −0.25955 | 0 |
| g__Granulicatella | NON-CRITICAL | −1.191 | 0.754242 | 0.027522 | 0 |
| g__Porphyromonas | NON-CRITICAL | −1 | 0.810755 | −0.05267 | 0 |
| g__Peptostreptococcus | NON-CRITICAL | −0.178 | 0.82805 | −0.15027 | 0 |
| g__Atopobium | NON-CRITICAL | −0.442 | 0.887095 | 0.00531 | 0 |
| g__Moryella | NON-CRITICAL | −0.239 | 0.903232 | −0.08963 | 0 |
| g__Bulleidia | NON-CRITICAL | −0.227 | 0.932681 | −0.57024 | 0 |
| g__Haemophilus | NON-CRITICAL | −0.809 | 0.934724 | 0.065274 | 0 |
| g__Gemella | NON-CRITICAL | −0.492 | 0.936951 | −0.21097 | 0 |
| g__Fusobacterium | NON-CRITICAL | −0.678 | 0.984941 | −0.04963 | 0 |
| g__Enterobacter | NON-CRITICAL | 0.029 | 0.991025 | −0.73606 | 0 |
| g__Oribacterium | NON-CRITICAL | −0.492 | 0.997194 | 0.090524 | 0 |
| g__Rothia | NON-CRITICAL | −0.083 | 0.997334 | −0.04905 | 0 |
| g__Actinomyces | NON-CRITICAL | 0.383 | 0.999346 | −0.22707 | 0 |
| g__Prevotella | NON-CRITICAL | −0.256 | 0.999923 | 0.161038 | 0 |
| g__Campylobacter | NON-CRITICAL | 0.467 | 0.999979 | −0.14546 | 0 |
| g__Veillonella | NON-CRITICAL | 0.508 | 0.999997 | −0.14545 | 0 |
| g__Propionibacterium | NON-CRITICAL | −2 | 1 | 0.813492 | 0 |
| g__Aggregatibacter | EXCLUSIVE | −1.9 | 'NA' | 'NA' | 'NA' |

Moreover, Table 5 shows various microbe along with their critical NESH value, the data-set where it was identified, the corresponding literature evidence summary, the source of the literature evidence and their morphology:

TABLE 5 various microbe along with their critical NESH value

| Microbe | Crtical NESH score | Data-set | Literature evidence | PMID | Cell-Shape | Gram-Staining | OxyReq | Sporulation |
|---|---|---|---|---|---|---|---|---|
| Ralstonia | −2.205942397 | I | Ralstonia colonization/infection occasionally reported by hospitals has generated increased interest in an organism previously little known to most clinicians | http://www.ncbi.nlm.nih.gov/pmc/articles/PMC4086841/ | Rod | Gram-Negative | Aerobe | Nonsporulating |
| TG5 | −1.418841239 | I | NA | NA | NA | NA | NA | NA |
| Peptostreptococcus | −1.322618418 | I | Recently reported to be associated with HIV infection | http://www.ncbi.nlm.nih.gov/pubmed/16887655 | Sphere | Gram-Positive | Anaerobe | Nonsporulating |
| Delftia | −1.195142166 | I | Believed to be non pathogenic usually; But Delftia acidovorans has been implicated in endocarditis and bacteremia. As such, the identification of Delftia sp. as a 'driver' bears close scrutiny whether or not this organism contributes to HIV. Fatal Delftia acidovorans infection in an immunocompetent patient has been reported. | http://www.ncbi.nlm.nih.gov/pubmed/2298872/ http://www.ncbi.nlm.nih.gov/pubmed/7811890/ http://www.ncbi.nlm.nih.gov/pubmed/20628778/ http://www.ncbi.nlm.nih.gov/pmc/articles/PMC3609244/ | Rod | Gram-Negative | Aerobe | NA |
| Porphyromonas | −0.903986159 | I | Known as a pathogen for periodontitis and cystic fibrosis. Periodontal diseases are reported to be strongly associated with HIV infection (http://www.ncbi.nlm.nih.gov/pubmed/21029260). | http://www.ncbi.nlm.nih.gov/pubmed/20610663 http://www.ncbi.nlm.nih.gov/pubmed/21151003 http://www.ncbi.nlm.nih.gov/pubmed/21029260 | Rod | Gram-Negative | Anaerobe | Nonsporulating |
| Moryella | −0.821943982 | I | No pathogenic associations reported | NA | Rod | Gram-Positive | Anaerobe | Nonsporulating |
| Bulleidia | −0.80775719 | I | One of the causative agent in a primary lung abscess | http://www.ncbi.nlm.nih.gov/pubmed/25387555 | Rod | Gram-Positive | Anaerobe | Nonsporulating |
| Staphylococcus | −0.746701244 | I | In persons infected with the human immunodeficiency virus (HIV), Staphylococcus aureus (S. aureus) infections account for significant morbidity | http://www.ncbi.nlm.nih.gov/pubmed/3400693/ | Sphere | Gram-Positive | Aerobe | Nonsporulating |
| Lactobacillus | −0.731290451 | I | Known to have roles in blocking HIV-1 transmission using cell surface protein. Although rarely a pathogen in humans, evidences exist for its role in Lung abscess and pleuritis | http://www.ncbi.nlm.nih.gov/pubmed/23318049 http://www.ncbi.nlm.nih.gov/pubmed/20072798 | Rod | Gram-Negative | Facultative | Nonsporulating |
| Eubacterium | −0.680177375 | I | Associated vaguely as periodontal pathogen | http://www.ncbi.nlm.nih.gov/pubmed/2304064 | Coccus | Gram-Positive | Anaerobe | Nonsporulating |
| Catonella | −0.648027423 | I | associated with cystic fibrosis | http://www.ncbi.nlm.nih.gov/pubmed/21151003 | Rod | Gram-Negative | Anaerobe | Nonsporulating |
| Selenomonas | −0.568443836 | I | reported to be associated with lung abscesses giving rise to fatal | http://www.ncbi.nlm.nih.gov/pubmed/4018070 | Rod | Gram-Positive | Anaerobe | Nonsporulating |

TABLE 5-continued various microbe along with their critical NESH value

| Microbe | Crtical NESH score | Data-set | Literature evidence | PMID | Cell-Shape | Gram-Staining | OxyReq | Sporulation |
|---|---|---|---|---|---|---|---|---|
| Streptococcus | −0.311028369 | I | septicemia in an immunocompromised patient Well known pulmonary pathogen and confirmed HIV association | http://www.ncbi.nlm.nih.gov/pubmed/8824970 | Coccus | Gram-Positive | Facultative anaerobe | Nonsporulating |
| Tropheryma | −1.848968111 | C | Reported to have widespread colonization and the etiologic agent of Whipple's disease | http://www.ncbi.nlm.nih.gov/pubmed/23392441 | Rod | Gram-Positive | Aerobe | Nonsporulating |
| Peptostreptococcus | −1.758546861 | C | Recently reported to be associated with HIV infection | http://www.ncbi.nlm.nih.gov/pubmed/16887655 | Sphere | Gram-Positive | Anaerobe | Nonsporulating |
| Moryella | −1.496081667 | C | No pathogenic associations reported | NA | Rod | Gram-Positive | Anaerobe | Nonsporulating |
| Neisseria | −0.762875355 | C | Known to facilitate HIV transmission and enhance HIV infection | http://www.ncbi.nlm.nih.gov/pubmed/22384840 http://www.ncbi.nlm.nih.gov/pubmed/20147631 | Coccus | Gram-Negative | Aerobe | Nonsporulating |

Microbial co-occurrence networks account to be a valuable method for visualizing and studying changes in association pattern that otherwise remains undisclosed by differential abundance analyses. In an ecological system, composed of closely interlinked entities influencing the behavior of each other, an approach that gives importance to connected perturbations hence holds a greater biological relevance. One of the important properties observed in the majority of these networks is the rewiring of nodes to give rise to a distinct set of edges in disease and healthy states while the participating nodes remain equivalent. The underlying reason that can be attributed to this phenomenon may be an ecological pressure owing to viral load that tries to adjust the equilibrium (analogous to Le Châtelier's principle in chemical equilibrium) by keeping the entities intact. An alternative perspective might point towards a conscious effort from the microbiome itself, lead by some key members (opportunist pathogens in case of disease), to assist the infectious agent. To correlate these findings, it was further explored the metadata corresponding to the datasets and calculated the average viral load for each study which indeed correlated with our cumulative NESH score and total 'driver' nodes. The absence of any 'driver' genera in the Penn [P] dataset probably pertains to its low viral load while the Indiana [I] dataset showed a high number of 'driver' taxa owing to the high viral load.

The written description describes the subject matter herein to enable any person skilled in the art to make and use the embodiments. The scope of the subject matter embodiments is defined by the claims and may include other modifications that occur to those skilled in the art. Such other modifications are intended to be within the scope of the claims if they have similar elements that do not differ from the literal language of the claims or if they include equivalent elements with insubstantial differences from the literal language of the claims.

It is, however to be understood that the scope of the protection is extended to such a program and in addition to a computer-readable means having a message therein; such computer-readable storage means contain program-code means for implementation of one or more steps of the method, when the program runs on a server or mobile device or any suitable programmable device. The hardware device can be any kind of device which can be programmed including e.g. any kind of computer like a server or a personal computer, or the like, or any combination thereof. The device may also include means which could be e.g. hardware means like e.g. an application-specific integrated circuit (ASIC), a field-programmable gate array (FPGA), or a combination of hardware and software means, e.g. an ASIC and an FPGA, or at least one microprocessor and at least one memory with software modules located therein. Thus, the means can include both hardware means and software means. The method embodiments described herein could be implemented in hardware and software. The device may also include software means. Alternatively, the embodiments may be implemented on different hardware devices, e.g. using a plurality of CPUs.

The embodiments herein can comprise hardware and software elements. The embodiments that are implemented in software include but are not limited to, firmware, resident software, microcode, etc. The functions performed by various modules described herein may be implemented in other modules or combinations of other modules. For the purposes of this description, a computer-usable or computer readable medium can be any apparatus that can comprise, store, communicate, propagate, or transport the program for use by or in connection with the instruction execution system, apparatus, or device.

The medium can be an electronic, magnetic, optical, electromagnetic, infrared, or semiconductor system (or apparatus or device) or a propagation medium. Examples of a computer-readable medium include a semiconductor or solid state memory, magnetic tape, a removable computer diskette, a random access memory (RAM), a read-only memory (ROM), a rigid magnetic disk and an optical disk. Current examples of optical disks include compact disk-read only memory (CD-ROM), compact disk-read/write (CD-R/W) and DVD.

A data processing system suitable for storing and/or executing program code will include at least one processor coupled directly or indirectly to memory elements through a system bus. The memory elements can include local memory employed during actual execution of the program code, bulk storage, and cache memories which provide temporary storage of at least some program code in order to reduce the number of times code must be retrieved from bulk storage during execution.

Input/output (I/O) devices (including but not limited to keyboards, displays, pointing devices, etc.) can be coupled to the system either directly or through intervening I/O controllers. Network adapters may also be coupled to the system to enable the data processing system to become coupled to other data processing systems or remote printers or storage devices through intervening private or public networks. Modems, cable modem and Ethernet cards are just a few of the currently available types of network adapters.

A representative hardware environment for practicing the embodiments may include a hardware configuration of an information handling/computer system in accordance with the embodiments herein. The system herein comprises at least one processor or central processing unit (CPU). The CPUs are interconnected via system bus to various devices such as a random access memory (RAM), read-only memory (ROM), and an input/output (I/O) adapter. The I/O adapter can connect to peripheral devices, such as disk units and tape drives, or other program storage devices that are readable by the system. The system can read the inventive instructions on the program storage devices and follow these instructions to execute the methodology of the embodiments herein.

The system further includes a user interface adapter that connects a keyboard, mouse, speaker, microphone, and/or other user interface devices such as a touch screen device (not shown) to the bus to gather user input. Additionally, a communication adapter connects the bus to a data processing network, and a display adapter connects the bus to a display device which may be embodied as an output device such as a monitor, printer, or transmitter, for example.

The preceding description has been presented with reference to various embodiments. Persons having ordinary skill in the art and technology to which this application pertains will appreciate that alterations and changes in the described structures and methods of operation can be practiced without meaningfully departing from the principle, spirit and scope.

What is claimed is:

1. A method for identification of key driver micro-organism responsible for bringing a change in a microbial population corresponding to a micro-biome associated disease in an individual, and determine a criticality score for the identified key driver micro-organism to correlate with a severity of viral load pertaining to the micro-biome associated disease in the individual, the method comprising a processor implemented steps of:

receiving, by an input module, a sample from a first set of individuals and a second set of individuals, wherein the first set of individuals are in a reference state and the second set of individuals are in a perturbed state, and wherein the reference state is a healthy state and the perturbed state is a diseased state corresponding to the micro-biome associated disease;

extracting, by an extractor, DNA samples from the sample from the first and the second set of individuals;

sequencing, by a sequencer, each of the DNA samples using a sequencer to generate a plurality of DNA sequences;

filtering and processing, by a processor, the plurality of DNA sequences for removing the low quality DNA sequences and non-essential DNA fragments;

creating, by the processor, two matrices of microbial abundance profile of the plurality of DNA sequences corresponding to the first set and the second set of individuals, wherein each matrix of microbial abundance profile includes abundances of microbial organisms corresponding to each members belonging to the microbial population;

normalizing, by the processor, each matrix using a normalization method;

representing, by the processor, microbial organisms in each matrix as a plurality of nodes;

generating, by CoNet plugin in Cytoscape network generation tool, a microbial association network for the first set and the second set using the normalized matrices, wherein each of the microbial association network comprises a plurality of nodes connected with more than 100 edges in the microbial association network;

computing, by the processor, Jaccard node index and Jaccard edge index between the microbial association network of first set and the microbial association network of the second set;

identifying, by the processor, if the Jaccard node index is higher than a first predefined value and the Jaccard edge index is lower than a second predefined value to confirm an occurrence of required network rewiring between the microbial association network of the first set and the microbial association network of the second set, wherein the first predefined value is any value between 0.6 and 1 and the second predefined value is any value between 0 and 0.6 confirming a high rewiring between the two sets with minimal addition or removal of another node; and when the Jaccard node index is higher than the first predefined value and the Jaccard edge index is lower than the second predefined value which confirms the occurrence of required network rewiring between the microbial association networks of the first set and the second set, perform computing, by the processor, a scaled change in betweenness for each of the nodes in the microbial association network of the second set with respect to the microbial association network of the first set, wherein the network rewiring of nodes gives rise to a distinct set of edges in the diseased and healthy states while the participating nodes remain equivalent due to an ecological pressure owing to viral load that tries to adjust equilibrium by keeping nodes intact;

after computing the scaled change in betweenness, calculating, by the processor, a neighbor shift score (NESH) for each of the nodes in the microbial association network of the second set with respect to the microbial association network of the first set using a predefined formula, wherein the neighbor shift score quantifies directional changes in the associations of each node in the microbial association network of the second set with respect to the microbial association network of the first set to distinguish between the healthy state and the diseased state, wherein the neighbor shift score enables identification of a key driver node involved in the network rewiring observed between the first set and the second set corresponding to the micro-biome associated disease, wherein calculation of the neighbor shift score (NESH) for the node using the predefined formula comprises:

evaluating the node present in both the reference and perturbed state based on a measure that calculates an extent of change in neighborhood similarity from the reference state to the diseased state comprising of three components namely:

a first component calculates an extent of node neighborhood similarity between the diseased and the healthy set normalized over all first neighbors in both the healthy and the diseased set combined;

a second component calculates a count of exclusive set of first interacting partners of considered node present in the diseased set normalized over the diseased set only; and a third component calculates the count of exclusive set of first interacting partners of the considered node normalized over all first neighbors in both the healthy and the diseased set combined; and computing the neighbor shift score (NESH) by subtraction of the combined value of the second and third components from the first component;

after calculating, the neighbor shift score (NESH), calculating, by the processor, a statistical significance value for the neighbor shift score for each of the nodes; and after calculating, the statistical significance value, identifying, by the processor, one or more nodes as the key driver micro-organisms if the statistical significance value of its neighbor shift score is less than a third predefined value and the scaled change in betweenness is positive, wherein the third predefined value is less than or equal to 0.1, wherein the identified one or more nodes are highly rewired and the key driver micro-organisms are responsible for bringing the change in the microbial population corresponding to the micro-biome associated disease, calculating a criticality score $NESH_{critical}$ for each of the identified nodes as the key driver micro-organisms, wherein the criticality score for the identified node is calculated based on the NESH value, a statistical significance probability (p) of the NESH value and the scaled increase in betweenness ($\Delta B''$) value of the identified node in the diseased set using equation $$NESH_{critical} = NESH*(1-p)*(1+\Delta B'')$$

wherein 'n' is a number of the identified node;

calculating a cumulative critical score by summing up the individual criticality score of each of the identified nodes; and using the cumulative critical score as an indicator for correlating with the severity of viral load pertaining to the micro-biome associated disease in the individual who is in the diseased state.

2. The method of claim 1, wherein the normalization method is a cumulative sum scaling method.

3. The method of claim 1 further comprises computing the scaled change in betweenness for each of the nodes in the microbial association network of second set of individuals with respect to the microbial association network of the first set of individuals, wherein scaled betweenness ($B_{scaled}$) for each of the nodes in both of the networks is computed using the formula:

$$B_{scaled} = B_{calculated} B_{min} / B_{max} - B_{min},$$

wherein $B_{calculated}$, $B_{min}$ and $B_{max}$ correspond to the calculated, min and max betweenness values of each of the nodes, and the scaled change in betweenness ($\Delta B''$) is computed for each of the common nodes of the microbial association network of the second set of individuals with respect to the microbial association network of the first set of individuals by using the formula:

$$\Delta B'' = B_{scaled}{}^n{}_D - B_{scaled}{}^n{}_H,$$

wherein $B_{scaled}{}^n{}_D$ and $B_{scaled}{}^n{}_H$ correspond to the scaled betweenness of node 'n' in diseased and healthy state respectively, wherein the nodes with a p-value less than or equal to 0.1 and a positive scaled change in betweenness ($\Delta B''$) are identified as the key driver micro-organisms.

4. A system for identification of key driver micro-organism responsible for bringing changes in a microbial population corresponding to a micro-biome associated disease in an individual, and determine a criticality score for the identified key driver micro-organism which correlate with a severity of viral load pertaining to the micro-biome associated disease in the individual, the system comprises:
   an input module for receiving a sample from a first set of individuals and a second set of individuals, wherein the first set of individuals are in a reference state and the second set of individuals are in a perturbed state, and wherein the reference state is a healthy state and the perturbed state is a diseased state corresponding to the micro-biome associated disease;
   an extractor for extracting DNA samples from the sample from the first and the second set of individuals;
   a sequencer for sequencing each of the DNA samples to generate a plurality of DNA sequences;
   a CoNet plugin in Cytoscape network generation tool for generating a microbial association network using abundances of microbial organisms corresponding to each member of a microbial population;
   a memory; and
   a processor coupled with the memory, wherein the processor configured to perform the steps of:
      filtering and processing the plurality of DNA sequences for removing the low quality DNA sequences and non-essential DNA fragments using a filtering module;
      creating two matrices of microbial abundance profile of the plurality of DNA sequences corresponding to the first set and the second set of individuals, wherein each matrix of microbial abundance profile includes abundances of microbial organisms corresponding to each members belonging to the microbial population;
      normalizing each matrix using a normalization method;
      representing microbial organisms in each matrix as a plurality of nodes;
      generating a microbial association network using the CoNet plugin in Cytoscape network generation tool for the first set and the second set of individuals using the normalized matrices, wherein each of the microbial association network comprises a plurality of nodes connected with more than 100 edges in the microbial association network;
      computing Jaccard node index and Jaccard edge index between the microbial association network of first set and the microbial association network of the second set;
      identifying if the Jaccard node index is higher than a first predefined value and the Jaccard edge index is lower than a second predefined value to confirm an occurrence of required network rewiring between the microbial association network of the first set and the microbial association network of the second set, wherein the first predefined value is any value between 0.6 and 1 and the second predefined value is any value between 0 and 0.6 confirming a high rewiring between the two sets with minimal addition or removal of another node;
      when the Jaccard node index is higher than the first predefined value and the Jaccard edge index is lower than the second predefined value which confirms the occurrence of required network rewiring between the microbial association networks of the first set and the second set, perform computing a scaled change in betweenness for each of the nodes in the microbial association network of second set with respect to the microbial association network of the first set, wherein the network rewiring of nodes gives rise to a distinct set of edges in the diseased and healthy states while the participating nodes remain equivalent due to an ecological pressure owing to viral load that tries to adjust equilibrium by keeping nodes intact;
      after computing the scaled change in betweenness, calculating a neighbor shift score (NESH) for each of the nodes in the microbial association network of the second set with respect to the microbial association network of the first set using a predefined formula, wherein the neighbor shift score quantifies directional changes in the associations of each node in the microbial association network of the second set with respect to the microbial association network of the first set to distinguish between the healthy state and the diseased state, wherein the neighbor shift score enables identification of a key driver node involved in the network rewiring observed between the first set and the second set corresponding to the micro-biome associated disease, wherein the calculation of the neighbor shift score (NESH) for the node using the predefined formula comprises:
         evaluating the node present in both the reference and perturbed state based on a measure that calculates the extent of change in neighborhood similarity from the reference state to the perturbed state comprising of three components namely:
            a first component that calculates the extent of node neighborhood similarity between the perturbed and the reference set normalized over all first neighbors in both the reference and the perturbed set combined;
            a second component that calculates the count of exclusive set of first interacting partners of the considered node present in the perturbed set normalized over the disease set only; and
            a third component that calculates the count of exclusive set of first interacting partners of the considered node normalized over all first neighbors in both the reference and the perturbed set combined; and computing the neighbor shift score (NESH) by subtraction of the combined value of second and third component from the first component;

after calculating, the neighbor shift score (NESH), calculating a statistical significance value for the neighbor shift score for each of the nodes; and after calculating, the statistical significance value, identifying one or more nodes as the key driver micro-organisms if the statistical significance value of its neighbor shift score is less than a third predefined value and the scaled change in betweenness is positive, wherein the third predefined value is less than or equal to 0.1, wherein the identified one or more nodes are highly rewired, and wherein the key driver micro-organisms are responsible for bringing the change in the microbial population corresponding to the micro-biome associated disease, calculating a criticality score $NESH_{critical}$ for the identified node as the key driver micro-organism, wherein the criticality score for the identified node is calculated based on the NESH value, a statistical significance probability (p) of the NESH value and the scaled increase in betweenness ($\Delta B''$) value of the identified node in the diseased set using equation $$NESH_{critical} = NESH*(1-p)*(1+\Delta B'')$$

wherein 'n' is a number of the identified node;

calculating a cumulative critical score by summing up the individual criticality score of each of the identified nodes; and using the cumulative critical score as an indicator for correlating with the severity of viral load pertaining to the micro-biome associated disease in the individual who is in the diseased state.

5. The system of claim 4, wherein the processor is further configured to compute the scaled change in betweenness for each of the nodes in the microbial association network of second set of individuals with respect to the microbial association network of the first set of individuals, wherein scaled betweenness ($B_{scaled}$) for each of the nodes in both of the networks is computed using the formula:

$$B_{scaled} = B_{calculated} - B_{min}/B_{max} - B_{min},$$

wherein $B_{calculated}$, $B_{min}$ and $B_{max}$ correspond to the calculated, min and max betweenness values of each of the nodes, and the scaled change in betweenness ($\Delta B''$) is computed for each of the common nodes of the microbial association network of the second set of individuals with respect to the microbial association network of the first set of individuals by using the formula:

$$\Delta B'' = B_{scaled}{}^n{}_D - B_{scaled}{}^n{}_H,$$

wherein $B_{scaled}{}^n{}_D$ and $B_{scaled}{}^n{}_H$ correspond to the scaled betweenness of node 'n' in diseased and healthy state respectively, wherein the nodes with a p-value less than or equal to 0.1 and a positive scaled change in betweenness ($\Delta B''$) are identified as the key driver micro-organisms.

6. A non-transitory computer-readable medium having embodied thereon a computer program executed by a processor for identification of key driver micro-organism responsible for bringing a change in a microbial population corresponding to a micro-biome associated disease in an individual, and determine a criticality score for the identified key driver micro-organism which to correlate with a severity of viral load pertaining to the micro-biome associated disease in the individual, the method comprising:

getting, by an input module, a sample from a first set of individuals and a second set of individuals, wherein the first set of individuals are in a reference state and the second set of individuals are in a perturbed state, and wherein the reference state is a healthy state and the perturbed state is a diseased state corresponding to the micro-biome associated disease;

extracting, by an extractor, DNA samples from the sample from the first and the second set of individuals;

sequencing, by a sequencer, each of the DNA samples using a sequencer to generate a plurality of DNA sequences;

filtering and processing, by a processor, the plurality of DNA sequences for removing the low quality DNA sequences and non-essential DNA fragments;

creating, by the processor, two matrices of microbial abundance profile of the plurality of DNA sequences corresponding to the first set and the second set of individuals, wherein each matrix of microbial abundance profile includes abundances of microbial organisms corresponding to each members belonging to the microbial population;

normalizing, by the processor, each matrix using a normalization method;

representing, by the processor, microbial organisms in each matrix as a plurality of nodes;

generating, by CoNet plugin in Cytoscape network generation tool, a microbial association network for the first set and the second set using the normalized matrices, wherein each of the microbial association network comprises a plurality of nodes connected with more than 100 edges in the microbial association network;

computing, by the processor, Jaccard node index and Jaccard edge index between the microbial association network of first set and the microbial association network of the second set;

identifying, by the processor, if the Jaccard node index is higher than a first predefined value and the Jaccard edge index is lower than a second predefined value to confirm an occurrence of required network rewiring between the microbial association network of the first set and the microbial association network of the second set, wherein the first predefined value is any value between 0.6 and 1 and the second predefined value is any value between 0 and 0.6 confirming a high rewiring between the two sets with minimal addition or removal of another node;

when the Jaccard node index is higher than the first predefined value and the Jaccard edge index is lower than the second predefined value which confirms the occurrence of required network rewiring between the microbial association networks of the first set and the second set, then perform computing, by the processor, a scaled change in betweenness for each of the nodes in the microbial association network of the second set with respect to the microbial association network of the first set, wherein the network rewiring of nodes gives rise to a distinct set of edges in the diseased and healthy states while the participating nodes remain equivalent due to an ecological pressure owing to viral load that tries to adjust equilibrium by keeping nodes intact;

after computing the scaled change in betweenness, calculating, by the processor, a neighbor shift score (NESH) for each of the nodes in the microbial association network of the second set with respect to the microbial association network of the first set using a predefined formula, wherein the neighbor shift score quantifies directional changes in the associations of each node in the microbial association network of the second set with respect to the microbial association network of the first set to distinguish between the healthy state and the diseased state, wherein the neighbor shift score enables identification of a key driver node involved in the network rewiring observed between the first set and the second set corresponding to the micro-biome associated disease, wherein the calculation of the neighbor shift score (NESH) for the node using the predefined formula comprises:

evaluating the node present in both the reference and perturbed state based on a measure that calculates the extent of change in neighborhood similarity from the reference state to the perturbed state comprising of three components namely:
- a first component that calculates the extent of node neighborhood similarity between the perturbed and the reference set normalized over all first neighbors in both the reference and the perturbed set combined;
- a second component that calculates the count of exclusive set of first interacting partners of the considered node present in the perturbed set normalized over the disease set only; and
- a third component that calculates the count of exclusive set of first interacting partners of the considered node normalized over all first neighbors in both the reference and the perturbed set combined; and computing the neighbor shift score (NESH) by subtraction of the combined value of second and third component from the first component;

after calculating, the neighbor shift score (NESH), calculating, by the processor, a statistical significance value for the neighbor shift score for each of the nodes; and after calculating, the statistical significance value, identifying, by the processor, one or more nodes as the key driver micro-organisms if the statistical significance value of its neighbor shift score is less than a third predefined value and the scaled change in betweenness is positive, wherein the third predefined value is less than or equal to 0.1, wherein the identified one or more nodes are highly rewired, and wherein the key driver micro-organisms are responsible for bringing the change in the microbial population corresponding to the micro-biome associated disease, calculating a criticality score $NESH_{critical}$ for the identified node as the key driver micro-organism, wherein the criticality score for the identified node is calculated based on the NESH value, a statistical significance probability (p) of the NESH value and the scaled increase in betweenness ($\Delta B''$) value of the identified node in the disease diseased set using equation $$NESH_{critical} = NESH*(1-p)*(1+\Delta B^n)$$

wherein 'n' is a number of the identified node;

calculating a cumulative critical score by summing up the individual criticality score of each of the identified nodes; and using the cumulative critical score as an indicator for correlating with severity of viral load pertaining to the micro-biome associated disease in the individual who is in the diseased state.

* * * * *